United States Patent
Niemeyer

(10) Patent No.: US 7,574,250 B2
(45) Date of Patent: *Aug. 11, 2009

(54) IMAGE SHIFTING APPARATUS AND METHOD FOR A TELEROBOTIC SYSTEM

(75) Inventor: Gunter D. Niemeyer, Mountain View, CA (US)

(73) Assignee: Intuitive Surgical, Inc., Sunnyvale, CA (US)

( * ) Notice: Subject to any disclaimer, the term of this patent is extended or adjusted under 35 U.S.C. 154(b) by 1016 days.

This patent is subject to a terminal disclaimer.

(21) Appl. No.: 10/358,608

(22) Filed: Feb. 4, 2003

(65) Prior Publication Data

US 2003/0114962 A1    Jun. 19, 2003

Related U.S. Application Data

(63) Continuation of application No. 09/457,406, filed on Dec. 7, 1999, now Pat. No. 6,799,065.

(60) Provisional application No. 60/111,711, filed on Dec. 8, 1998.

(51) Int. Cl.
*A61B 5/05* (2006.01)
*G06F 19/00* (2006.01)
*G05B 19/18* (2006.01)
*B25J 9/18* (2006.01)
*G05B 19/19* (2006.01)

(52) U.S. Cl. .................. 600/427; 600/407; 600/417; 901/32; 700/245; 700/251; 318/568.11

(58) Field of Classification Search ............... 600/417; 901/32; 700/245, 251; 318/568.11
See application file for complete search history.

(56) References Cited

U.S. PATENT DOCUMENTS

| | | |
|---|---|---|
| 4,672,963 A | 6/1987 | Barken |
| 4,722,056 A | 1/1988 | Roberts et al. |
| 4,791,934 A | 12/1988 | Brunnett |
| 4,837,703 A | 6/1989 | Kakazu et al. |
| 4,858,149 A | 8/1989 | Quarendon |
| 4,984,157 A | 1/1991 | Cline et al. |
| 5,079,699 A | 1/1992 | Tuy et al. |
| 5,086,401 A | 2/1992 | Glassman et al. |
| 5,098,426 A | 3/1992 | Sklar et al. |
| 5,099,846 A | 3/1992 | Hardy |
| 5,142,930 A | 9/1992 | Allen et al. |
| 5,170,347 A | 12/1992 | Tuy et al. |
| 5,182,641 A | 1/1993 | Diner et al. |
| 5,230,338 A | 7/1993 | Allen et al. |

(Continued)

OTHER PUBLICATIONS

Adams et al., "Computer-assisted surgery" IEEE Computer Graphics and Applications (May 1990) pp. 43-51.

(Continued)

*Primary Examiner*—Brian Casler
*Assistant Examiner*—Parikha S Mehta

(57) ABSTRACT

An input device of a teleoperator system can be operatively associated with an image of a surgical worksite. Movement of the image may correspond to movement of the input device so that the worksite image appears substantially connected to the input device. The operator can manipulate the worksite into a desired position, typically by repositioning of an image capture device. Dedicated input devices may be provided for a surgical instrument.

26 Claims, 21 Drawing Sheets

U.S. PATENT DOCUMENTS

| | | | |
|---|---|---|---|
| 5,230,623 | A | 7/1993 | Guthrie et al. |
| 5,235,510 | A | 8/1993 | Yamada et al. |
| 5,251,127 | A | 10/1993 | Raab |
| 5,257,203 | A | 10/1993 | Riley et al. |
| 5,261,404 | A | 11/1993 | Mick et al. |
| 5,368,428 | A | 11/1994 | Hussey et al. |
| 5,402,801 | A | 4/1995 | Taylor |
| 5,417,210 | A | 5/1995 | Funda et al. |
| 5,445,166 | A | 8/1995 | Taylor |
| 5,531,742 | A | 7/1996 | Barken |
| 5,631,973 | A | 5/1997 | Green |
| 5,695,500 | A | 12/1997 | Taylor et al. |
| 5,762,458 | A | 6/1998 | Wang et al. |
| 5,808,665 | A | 9/1998 | Green |
| 5,876,325 | A | 3/1999 | Mizuno et al. |
| 5,911,036 | A | 6/1999 | Wright et al. |
| 5,931,832 | A | 8/1999 | Jensen |
| 6,063,095 | A * | 5/2000 | Wang et al. ............... 606/139 |
| 6,096,025 | A | 8/2000 | Borders |
| 6,246,200 | B1 * | 6/2001 | Blumenkranz et al. . 318/568.11 |
| 6,459,926 | B1 * | 10/2002 | Nowlin et al. ............... 600/429 |

OTHER PUBLICATIONS

Askew et al., "Ground control testbed for space station freedom robot manipulators" IEEE Virtual Reality Annual International Symposium (Sep. 18-22, 1993), Seattle, Washington, pp. 69-75.

Bjura et al., "Merging virtual objects with the real world: Seeing ultrasound imagery within the patient" Computer Graphics 91992) 26(2):203-210.

Cao et al., "Task and motion analysis in endoscopic surgery" Submitted for Fifth Annual Symposium on Haptic Interfaces for Virutal; Environment and Teleoperator Systems for the Winter Meeting of ASME, (1996) pp. 1-32.

Christensen et al., "Model based, sensor directed remediation of underground storage tanks" Proceedings of the IEEE International Conference on Robotics and Automation (1991) pp. 1377-1383.

Dolan et al., "A robot in an operating room: A bull in a china shop?" IEEE/Ninth Annual Conference of the Engineering in Medicine and Biology Society (1987) 2 pages total.

Elder et al., "Specifying user interfaces for safety-critical medical systems" Second Annual International Symposium on Medical Robotics and Computer Assisted Surgery (1995) pp. 148-155.

Gayed et al., "An advanced control micromanipulator for surgical applications" Systems Science (1987) 13:123-133.

Harris et al., "A robotic procedure for transurethral resection of the prostate" Second Annual International Symposium on Medical Robotics and Computer Assisted Surgery (1995) pp. 264-271.

Hunter et al., "A teleoperated microsurgical robot and associated virtual environment for eye surgery" Presence Teleoperators and Virtual Environments, MIT Press (1993) 2(4):264-280.

Hunter et al., "Ophthalmic microsurgical robot and associated virtual environment" Comput. Biol. Med. (1995) 25(2):173-183.

Hurteau et al., "Labaroscopic surgery assisted by a robotic cameraman: Concept and experimental results" IEEE International Conference on Robotics and Automation (1994) pp. 2286-2289.

Jackson et al., "Force feedback and medical simulation" Interactive Technology and the New Paradigm (1995) pp. 147-151.

Kazerooni, "Design and analysis of the statically balanced direct-drive robot manipulator" Robotics and Computer-Integrated Manufacturing (1989) 6(4):287-293.

Kilmer et al., "Watchdog safety computer design and implementation" RI/SME Robots 8 Conference, (Jun. 1984) pp. 101-117.

Kosugi et al. "An articulated neurosurgical navigation system using MRI an CT Images" IEEE Transactions on Biomedical Engineering (1988) 35(2):147-152.

Ng et al., "Robotic surgery" IEEE Engineering in Medicine and Biology (1993) 120-125.

Paul et al., "Development of a surgical robot for cementless total hip arthroplasty" Clinical Orthopaedics and Related Research (1992) No. 285, pp. 57-66.

Preising et al., "A Literature Review: Robots in Medicine" IEEE Engineering in Medicine and Biology (Jun. 1991) pp. 13-22.

Rosenberg, "Human interface hardware for virtual laparoscopic surgery" Interactive Technology and the New Paradigm for Healthcare (1995) Morgan et al., Eds., pp. 322-325.

Schenker et al., :Development of a telemanipulator for dexterity enhanced microsurgery Second Annual International Symposium on Medical Robotics and Computer Assisted Surgery (1995) pp. 81-88.

Taylor et al., "A telerobotic assistant for laparoscopic surgery" IEEE Engineering in Medicine and Biology (1995) pp. 279-288.

Taylor et al., Research report: A telerobotic assistant for laparoscopic surgery Computer Science (1994) pp. 1-21.

Toon, "Eye surgery simulator could help physicians learn and practice new techniques" Research Horizons (Fall 1993) pp. 22-23.

Trivedi et al., "Developing telerobotic systems using virtual reality concepts" Proceedings of the 1993 IEEE/RSJ International Conference on Intelligent Robots and systems(1993) 8 pages total.

Vertut, Jean and Coeffet, Philippe; "Robot Technology; vol. 3a Teleoperation and Robotics Evolution and Development"; pp. 196-235.Prentice—Hall; Englewood Cliffs, NJ.

Vertut, Jean and Coiffet, Philippe; Teleoperations and Robotics: Evolution and Development;1986 ; pp. 211-220; Prentice—Hall; 1986.

* cited by examiner

IMAGE SHIFTING APPARATUS AND METHOD FOR A TELEROBOTIC SYSTEM

CROSS REFERENCE TO RELATED APPLICATIONS

This application is a continuation of U.S. application Ser. No. 09/457,406, filed Dec. 7, 1999, now U.S. Pat. No. 6,799,065, which claims the benefit of priority from U.S. Provisional Application No. 60/111,711, filed Dec. 8, 1998, the full disclosures of which is incorporated herein by reference.

BACKGROUND OF THE INVENTION

This invention relates to image shifting in a Telerobotic system, and more particularly, to robotically assisted methods and apparatus which are beneficial for use in surgery.

Minimally invasive medical techniques are aimed at reducing the amount of extraneous tissue which may be damaged during diagnostic or surgical procedures, thereby reducing patient recovery time, discomfort, and deleterious side effects. Many surgeries are performed each year in the United States. A significant amount of these surgeries can potentially be performed in a minimally invasive manner. However, only a relatively small percentage of surgeries currently use minimally invasive techniques due to limitations of minimally invasive surgical instruments and techniques currently used and the difficulty experienced in performing surgeries using such traditional instruments and techniques.

Advances in minimally invasive surgical technology could dramatically increase the number of surgeries performed in a minimally invasive manner. The average length of a hospital stay for a standard surgery is significantly longer than the average length for the equivalent surgery performed in a minimally invasive surgical manner. Thus, expansion in the use of minimally invasive techniques could save millions of hospital days, and consequently millions of dollars annually, in hospital residency costs alone. Patient recovery times, patient discomfort, surgical side effects, and time away from work can also be reduced by expanding the use of minimally invasive surgery.

Traditional forms of minimally invasive surgery include endoscopy. One of the more common forms of endoscopy is laparoscopy, which is minimally invasive inspection or surgery within the abdominal cavity. In traditional laparoscopic surgery a patient's abdominal cavity is insufflated with gas and cannula sleeves are passed through small (approximately ½ inch) incisions in the musculature of the patient's abdomen to provide entry ports through which laparoscopic surgical instruments can be passed in a sealed fashion.

The laparoscopic surgical instruments generally include a laparoscope for viewing the surgical field and working tools defining end effectors. Typical surgical end effectors include clamps, graspers, scissors, staplers, and needle holders, for example. The working tools are similar to those used in conventional (open) surgery, except that the working end or end effector of each tool is separated from its handle by an approximately 12-inch long extension tube, for example, so as to permit the surgeon to introduce the end effector to the surgical site and to control movement of the end effector relative to the surgical site from outside a patient's body.

To perform surgical procedures, the surgeon typically passes these working tools or instruments through the cannula sleeves to the internal surgical site and manipulates the instruments or tools from outside the abdomen by sliding them in and out through the cannula sleeves, rotating them in the cannula sleeves, levering (i.e., pivoting) the instruments against the abdominal wall and actuating the end effectors on the distal ends of the instruments from outside the abdominal cavity. The instruments normally pivot around centers defined by the incisions which extend through the muscles of the abdominal wall. The surgeon typically monitors the procedure by means of a television monitor which displays an image of the surgical site via the laparoscopic camera. Typically, the laparoscopic camera is also introduced through the abdominal wall so as to capture an image of the surgical site. Similar endoscopic techniques are employed in, e.g., arthroscopy, retroperitoneoscopy, pelviscopy, nephroscopy, cystoscopy, cisternoscopy, sinoscopy, hysteroscopy, urethroscopy, and the like.

There are many disadvantages relating to such traditional minimally invasive surgical (MIS) techniques. For example, existing MIS instruments deny the surgeon the flexibility of tool placement found in open surgery. Difficulty is experienced in approaching the surgical site with the instruments through the small incisions. The length and construction of many endoscopic instruments reduces the surgeon's ability to feel forces exerted by tissues and organs on the end effector of the associated instrument. Furthermore, coordination of the movement of the end effector of the instrument as viewed in the image on the television monitor with actual end effector movement is particularly difficult, since the movement as perceived in the image normally does not correspond intuitively with the actual end effector movement. Accordingly, dexterity and sensitivity of endoscopic tools has been found to be an impediment to the expansion of the use of minimally invasive surgery.

Minimally invasive telesurgical systems for use in surgery have been and are still being developed to increase a surgeon's dexterity as well as to permit a surgeon to operate on a patient in an intuitive manner. Telesurgery is a general term for surgical systems where the surgeon uses some form of remote control, e.g., a servomechanism, or the like, to manipulate surgical instrument movements, rather than directly holding and moving the tools by hand. In such a telesurgery system, the surgeon is typically provided with an image of the surgical site on a visual display at a location remote from the patient. The surgeon can typically perform the surgical procedure at the location remote from the patient whilst viewing the end effector movement during the surgical procedure on the visual display. While viewing typically a three-dimensional image of the surgical site on the visual display, the surgeon performs the surgical procedures on the patient by manipulating master control devices at the remote location, which master control devices control motion of the remotely controlled instruments.

Typically, such a telesurgery system can be provided with at least two master control devices (one for each of the surgeon's hands), which are normally operatively associated with two robotic arms on each of which a surgical instrument is mounted. Operative communication between master control devices and associated robotic arm and instrument assemblies is typically achieved through a control system. The control system typically includes at least one processor which relays input commands from the master control devices to the associated robotic arm and instrument assemblies and from the arm and instrument assemblies to the associated master control devices in the case of, e.g., force feedback, or the like.

To enhance the capabilities and acceptance of teleoperation systems, it is an object of the present invention to provide improved teleoperation methods, systems, and devices. It would be particularly beneficial to provide improved techniques for shifting an image shown to a system operator using a teleoperator system, especially for telesurgical applications.

It would further be beneficial if these improved techniques enhanced an operator's control over the system while modifying an image. It is an object of this invention to provide a method of performing an image shift while inhibiting the loss of the surgical instruments from the field of view of the endoscope.

BRIEF SUMMARY OF THE INVENTION

In a first aspect, the invention provides a method of preparing to perform or performing a procedure at a worksite with a robotic system. The method comprises capturing an image of the site with an image capture device. The captured image is displayed on an image display to be viewed by an operator of the robotic system. The operator is permitted to manipulate a master control, causing an end effector to perform at least a part of the procedure at the site. The master control is selectively caused to be operatively associated with the displayed image, and the displayed image is changed in response to manipulation of the master control.

In another aspect, the invention provides a surgical system for performing a surgical procedure at a surgical site on a patient body. The surgical system comprises an image capture device for capturing an image of the surgical site. An image display is coupled to the image capture device for displaying the captured image to an operator of the surgical system. An instrument arm has a mounting formation defined at one end, with a surgical end effector operatively mountable on the mounting formation. A master control is often coupled to a control system, with the control system arranged to permit the master control to be operatively associated with the surgical end effector so as to cause the surgical end effector to move and perform at least a part of the surgical procedure in response to manipulation of the master control, and also to permit the master control to be selectively operatively associated with the displayed image to enable the displayed image to be changed in response to manipulation of the master control.

In another aspect, the invention provides a method for preparing for or performing a procedure. The procedure comprises manipulating an object at a worksite per instructions of an operator. The method comprises showing an image of the object to the operator using a display. An input device is manipulated with a hand of the operator and the image shown on the display is moved in response to the manipulation of the input device so that the image of the object shown to the operator appears substantially connected to the input device.

In yet another aspect, the invention provides a robotically assisted surgical system. The surgical system comprises a display and an image of a tissue shown on the display. An input device is movable relative to the display. A processor couples the input device to the display. The processor effects movement of the image on the display in response to movement of the input device so that the tissue appears substantially connected to the input device.

In yet another aspect, the invention provides a telerobotic system comprising a viewer and a camera positionable at a remote site. The camera is mounted on a robotic arm to enable it to be positionally adjusted at the remote site. The camera is operatively associated with the viewer to enable an image of the remote site to be displayed on the viewer. A slave instrument or tool is positionable at the remote site. The tool is mounted on a robotic arm to enable it to be worked at the remote site. A master control device is in close proximity to the viewer to enable it to be manipulated by a user of the system while the user is viewing the remote site through the viewer. The master control device can selectively establish control over the robotic arm of the camera and to the robotic arm of the slave instrument so that positional adjustment of the camera and working of the tool can be effected by the master control.

In a still further aspect, the invention provides, for use with a robotic system (including a viewer operatively associated with a remote camera arrangement so as to display an image viewed by the camera on the viewer, and at least two master control devices each of which is operatively connected to a remote instrument or tool so as to cause displacement of the instrument or tool in response to displacement of its associated master control device) a method of shifting the image relative to the instrument or tool. The method comprises locking the instruments at stationary positions and moving the master control devices relative to the viewer while movement of the master control devices relative to each other is restrained. The camera is caused to displace relative to the instruments while the instruments are held at their stationary positions in response to the master control devices being displaced relative to the viewer.

A still further aspect provides a robotic surgical system comprising an image capture device for viewing a surgical workspace. A display is operatively coupled to the image capture device to show an image of the surgical workspace adjacent a controller workspace. The master controller is movable in the controller workspace. A surgical end effector is disposed in the surgical workspace. A processor couples the master controller to the image capture device and to the end effector. The processor has a first operating mode effecting movement to the surgical end effector such that the end effector in the image follows movement of the master controller in the controller workspace. The processor also has a second operating mode effecting movement to the image capture device so that the surgical workspace in the image follows movement of the master controller in the controller workspace.

In yet another aspect, the invention provides a telerobotic system comprising a viewer, an image capture device coupled to the viewer to produce an image of a workspace, and a robotic arm having an end effector disposed in the workspace. A processor couples the image capture device to the robotic arm so as to maintain an image of the end effector within the image of the workspace.

Other features and advantages of the invention will appear from the following description in which the preferred embodiment has been set forth in detail in conjunction with the accompanying drawings.

DETAILED DESCRIPTION OF THE INVENTION

Figure 1:
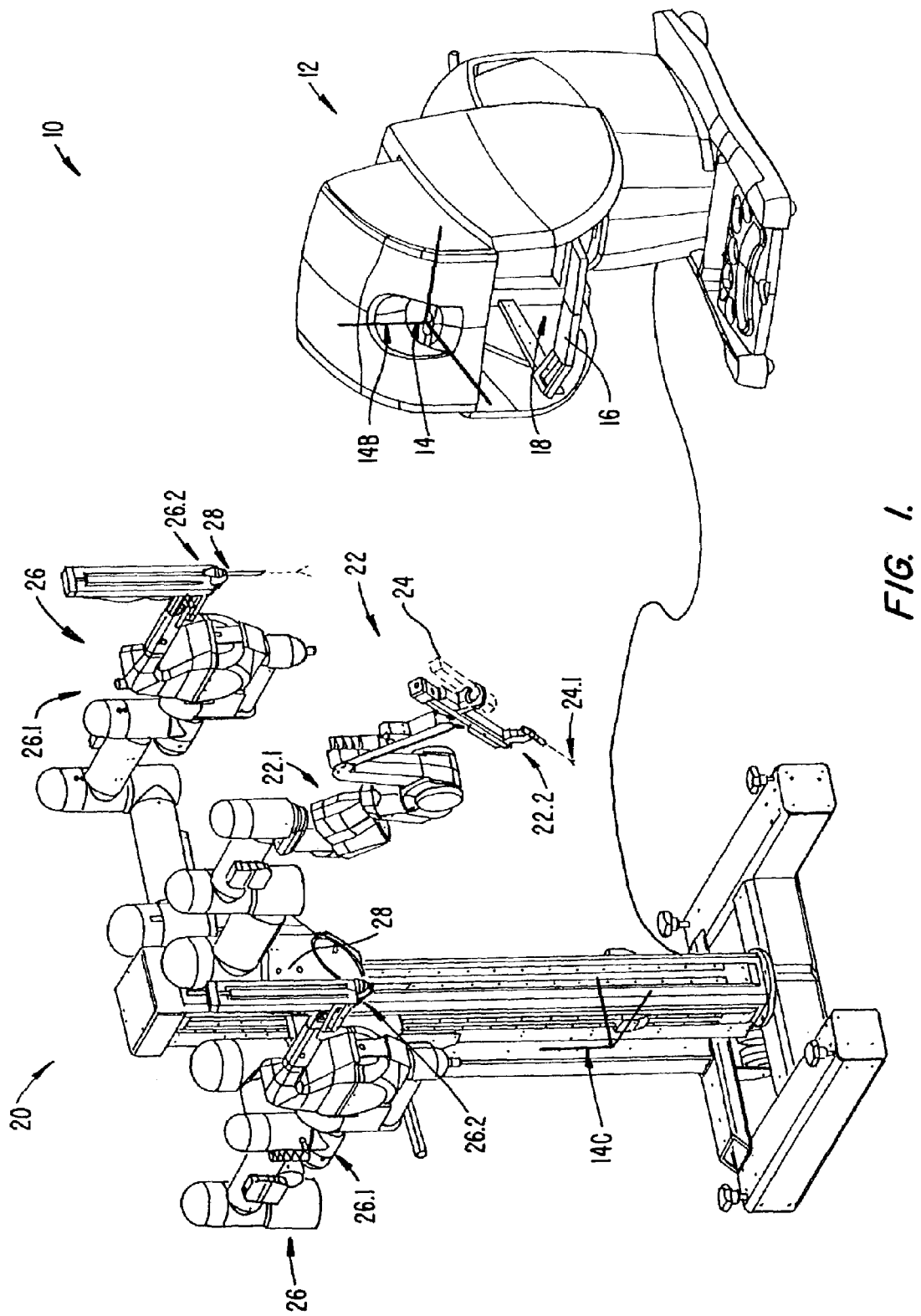
FIG. 1 shows a three-dimensional view of an operator control station, or surgeon's console, and a surgical work station, or cart, of a telesurgical system in accordance with the invention, the cart carrying three robotically controlled arms, the movement of the arms being remotely controllable from the control station.

Although this invention will now be described with reference to its application in the field of minimally invasive surgery, it is to be appreciated that the invention is not to be limited to use in this field only. It is envisaged that the invention can be applied in various fields using telerobotic systems. For example, the invention can be applied in telerobotic systems used to perform non-minimally invasive surgical procedures, or inspection procedures, or the like. The invention can also be applied in telerobotic systems used to handle hazardous substances, such as, nuclear fuel, nuclear waste, and the like. The invention can yet further be applied in telerobotic systems used in the manufacturing industry, for example, to assemble parts, to perform operations such as welding, and/or the like.

As used herein, objects (and/or images) appear "substantially connected" if a direction of an incremental positional movement of a first object matches the direction of an incremental positional movement of a second object (often as seen in an image). Matching directions need not be exactly equal, as the objects (or the object and the image) may be perceived as being connected if an angular deviation between the movements remains less than about ten degrees, preferably being less than about five degrees. Similarly, objects and/or images may be perceived as being "substantially and orientationally connected" if they are substantially connected and if the direction of an incremental orientational movement of the first object is matched by the direction of an incremental orientational movement of the second object (often as seen in an image displayed near the first object).

Additional levels of connectedness may, but need not, be provided. "Magnitude connection" indicates substantial connection and that the magnitude of orientational and/or positional movements of the first object and second object (typically as seen in an image) are directly related. The magnitudes need not be equal, so that it is possible to accommodate scaling and/or warping within a substantially magnitude connected robotic system. Orientational magnitude connection will imply substantial and orientational connection as well as related orientational movement magnitudes, while substantial and magnitude connection means substantial connection with positional magnitudes being related.

As used herein, a first object appears absolutely positionally connected with an image of a second object if the objects are substantially connected and the position of the first object and the position of the image of the second object appear to match, i.e., to be at the same location, during movement. A first object appears absolutely orientationally connected with an image of the second object if they are substantially connected and the orientation of the first object and the second object appear to match during movement.

The invention will now be described, by way of example, with reference to the accompanying diagrams.

Figure 6:
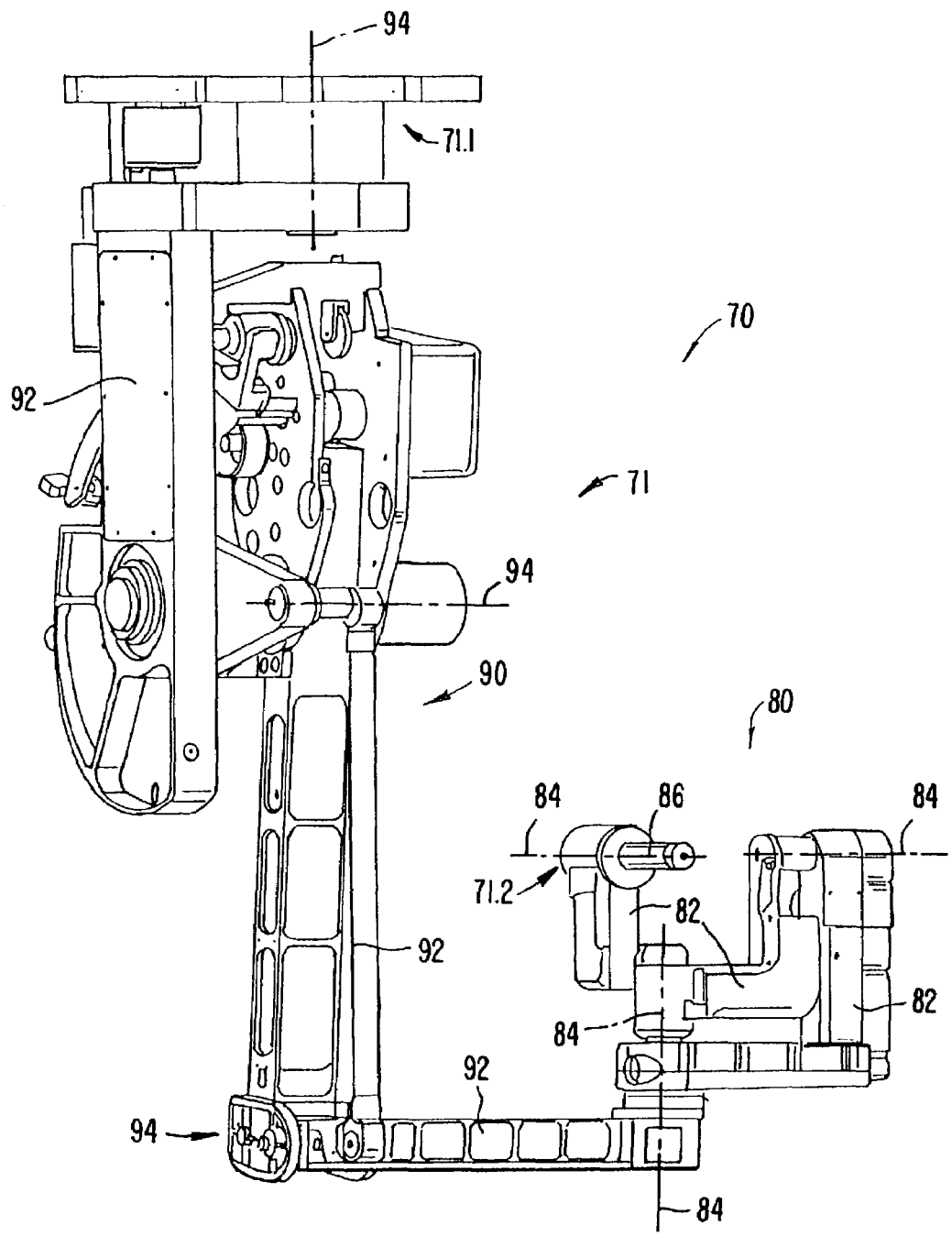
FIG. 6 shows a three-dimensional view of one of the master control devices of the control station shown in FIG. 1, the master control device including a hand-held part, or wrist gimbal, and an articulated arm portion on which the hand-held part is mounted.

In FIG. 1 of the drawings, a minimally invasive telesurgical system, or robotically controlled surgical system, in accordance with the invention, is generally indicated by reference numeral 10. The system 10 typically includes a control station, or surgeon's console, generally indicated by reference numeral 12. The station 12 includes an image display, or viewer, 14. An image of a surgical site is typically displayed on the image display 14, in use. A support 16 is provided on which an operator, typically a surgeon, can rest his or her forearms while gripping two master controls, one of which is shown in FIG. 6 of the drawings, one in each hand. The master controls are positioned in a space 18 inwardly beyond the support 16. When using the control station 12, the surgeon typically sits in a chair in front of the control station 12, positions his or her eyes in front of the viewer 14, and grips the master controls one in each hand, while resting his or her forearms on the support 16.

The system 10 further includes a surgical work station, or cart, generally indicated by reference numeral 20. In use, the cart 20 is positioned in close proximity to a patient requiring surgery and is then normally caused to remain stationary until a surgical procedure to be performed by means of the system 10 has been completed. The cart 20 typically has wheels or castors to render it mobile.

The cart 20 typically carries at least three arms. One of the arms, which will be referred to as a camera arm 22, is arranged to hold an image capture device 24, e.g., an endoscope, or the like. The camera arm 22 defines opposed ends 22.1, 22.2. The endoscope 24 is typically releasably mounted on the one end 22.2. The opposed end 22.1 of the arm 22 is connected to the cart 20. The arm 22 is movable to vary a location of the endoscope 24 relative to the opposed end 22.1 of the arm 22. Each of the other two arms, which will be referred to as instrument arms 26, 26, is arranged to hold a surgical instrument 28. The surgical instruments typically define end effectors, as described in greater detail below, for performing surgical tasks during a surgical procedure performed by means of the system 10. Each arm 26, 26 defines opposed ends 26.1, 26.2. The instruments, and accordingly also the end effectors, are typically releasably mounted on the ends 26.2, 26.2. The opposed ends 26.1, 26.1 of the arms 26, 26 are connected to the cart 20. The arms are movable to vary locations of the end effectors relative to the opposed ends 26.1, 26.1 of the arms 26, 26.

The endoscope 24 has an object viewing end 24.1 at a remote end of an elongate shaft thereof. It will be appreciated that the endoscope 24 has an elongate shaft to permit its viewing end 24.1 to be inserted through an entry port in a patient's body so as to access an internal surgical site. The endoscope 24 is typically operatively connected to the image display 14 so as to cause an image of the surgical site, captured at its viewing end 24.1, to be displayed on the image display 14.

Each instrument arm 26, 26 is normally operatively associated with one of the master controls during the performance of the surgical procedure, so as to enable the locations of the end effectors to be varied relative to the opposed ends 26.1, 26.1 of the arms 26, 26 in response to manipulation of their associated master controls. The end effectors are typically mounted on wrist members which are pivotally mounted on operatively distal ends of elongate shafts of the instruments 28 to enable the end effectors to be moved relative to the ends of the shafts. It will be appreciated that the instruments 28 have elongate shafts to permit the end effectors to be inserted through entry ports in a patient's body so as to access the internal surgical site. Movement of the end effectors relative to the ends of the shafts of the instruments 28, 28 is also controlled by the master controls.

When a surgical procedure is to be performed, the cart 20 carrying the arms 22, 26, 26 is typically wheeled to the patient and is normally maintained in a stationary position relative to, and in close proximity to, the patient, during the surgical procedure.

Figure 2:
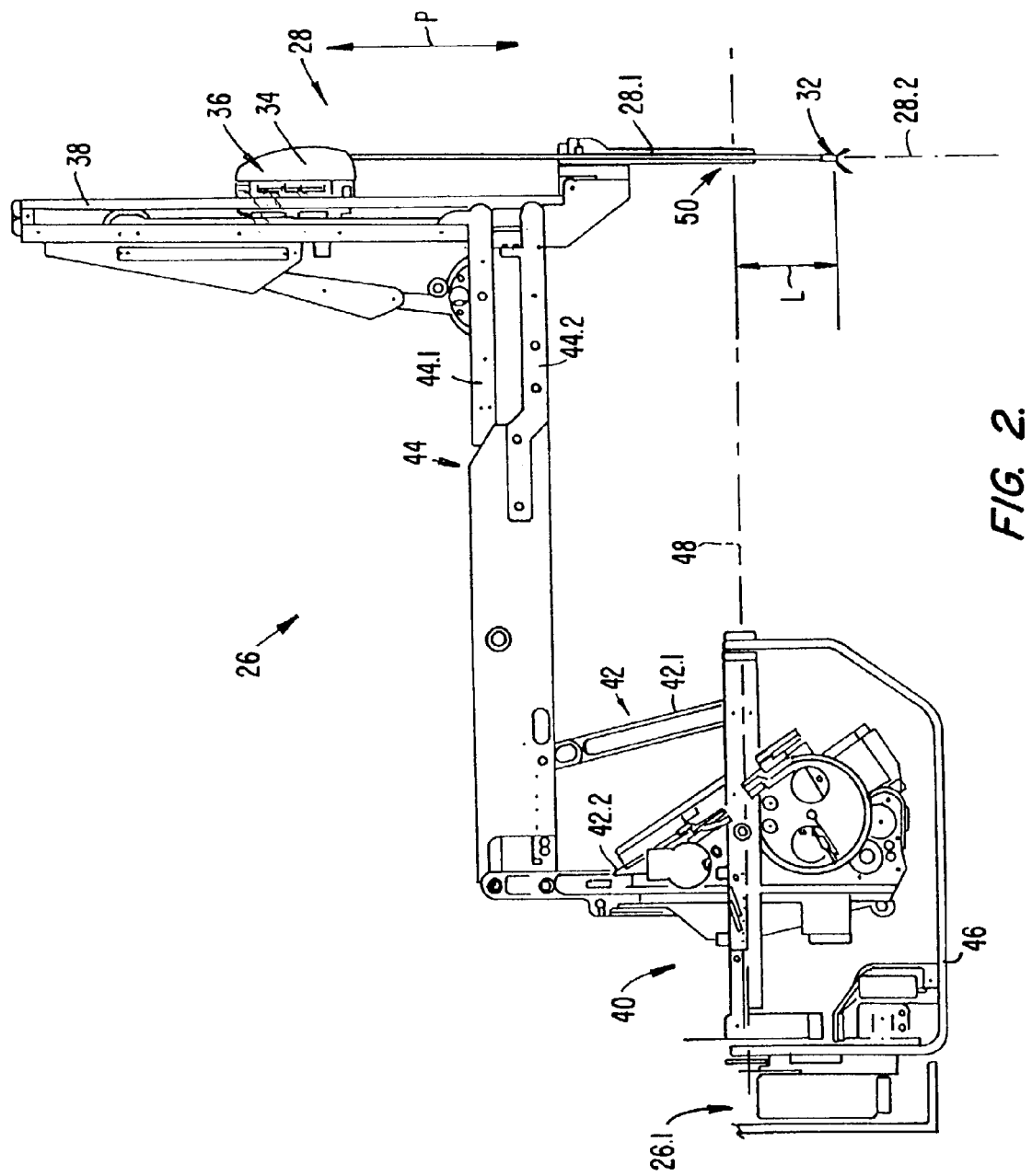
FIG. 2 shows, at an enlarged scale, a side view of a robotic arm and surgical instrument assembly of the surgical station shown in FIG. 1.
Figure 3:
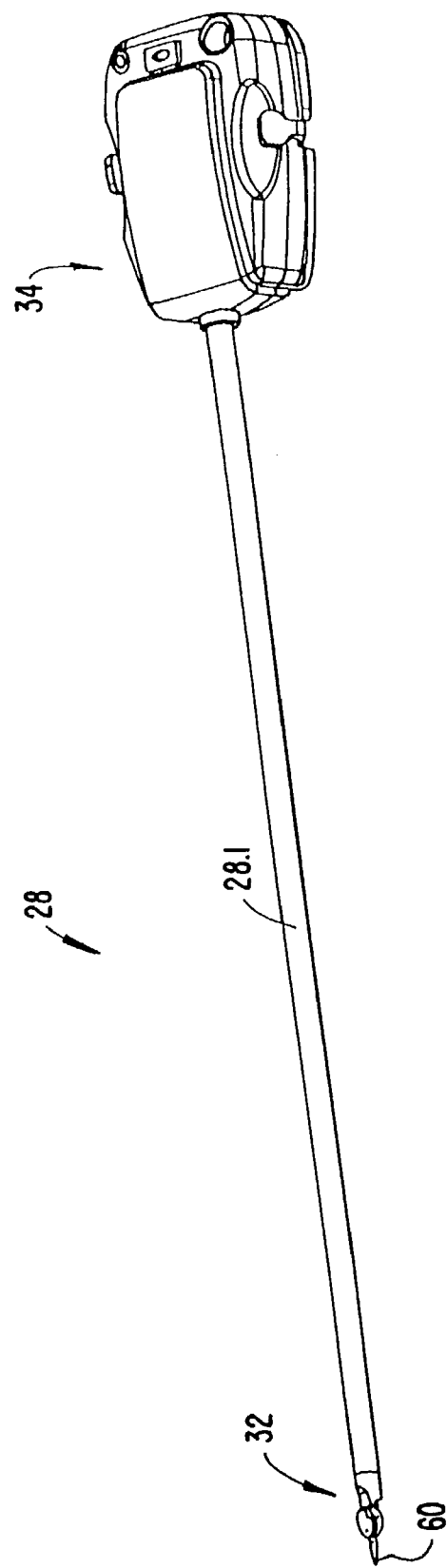
FIG. 3 shows, at an enlarged scale, a three-dimensional view of a typical surgical instrument of the system shown in FIG. 1.

In FIG. 2 of the drawings, one of the arms 26 is shown in greater detail, and on an enlarged scale. As mentioned, each arm 26 typically carries a surgical instrument. The surgical instrument mounted on the arm shown in FIG. 2 is schematically indicated at 28. FIG. 3 indicates the general appearance of a typical surgical instrument 28 in greater detail.

Referring now to FIG. 3 of the drawings, the elongate shaft of the surgical instrument 28 is indicated at 28.1. The wrist-like mechanism, generally indicated by reference numeral 32, is located at a working end of the shaft 28.1. A housing 34, arranged releasably to mount the instrument 28 on the arm 26, is located at an opposed end of the shaft 28.1. In FIG. 2, and when the instrument 28 is mounted on the arm 26, the shaft 28.1 extends along an axis indicated at 28.2. The instrument 28 is typically releasably mounted on a carriage 36, which can be driven to translate along a linear guide formation 38 of the arm 26 in the direction of arrows P.

The arm 26 includes a cradle, generally indicated at 40, an upper arm portion 42, a forearm portion 44, and the guide formation 38. The cradle 40 is pivotally mounted on a plate 46 in a gimbaled fashion to permit rocking movement of the cradle 40 about a pivot axis 48. The upper arm portion 42 includes link members 42.1, 42.2 and the forearm portion 44 includes link members 44.1, 44.2. The link members 42.1, 42.2 are pivotally mounted on the cradle 40 and are pivotally connected to the link members 44.1, 44.2. The link members 44.1, 44.2 are pivotally connected to the guide formation 38. The pivotal connections between the link members 42.1, 42.2, 44.1, 44.2, the cradle 40, and the guide formation 38 are arranged to constrain the robotic arm 26 to move in a specific manner relative to its opposed end 26.1. The movement of the robotic arm 26 is illustrated schematically in FIG. 4.

Figure 4:
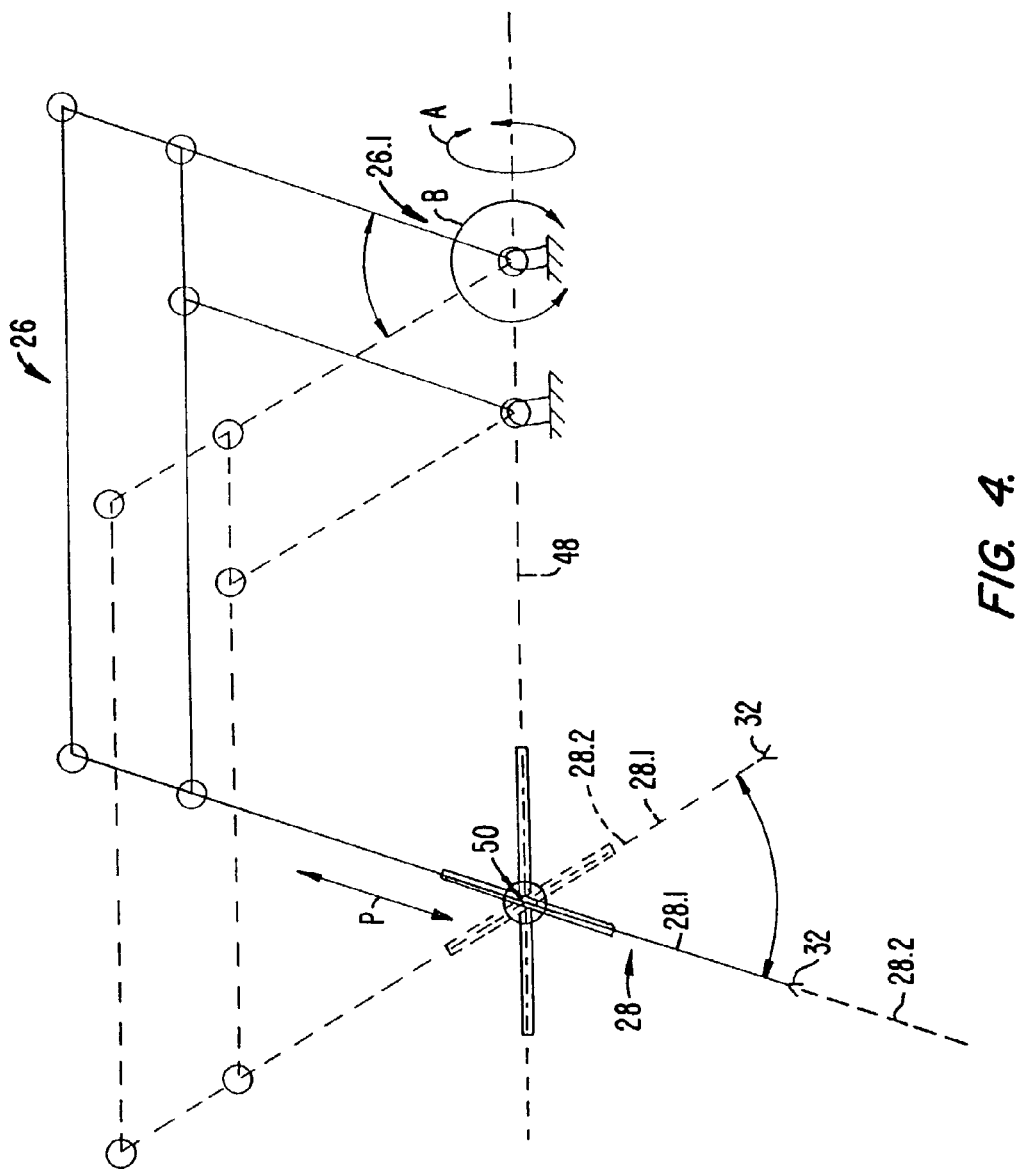
FIG. 4 shows a schematic kinematic diagram corresponding to the side view of the robotic arm shown in FIG. 2, and indicates the arm having been displaced from one position into another position.

With reference to FIG. 4 of the drawings, the solid lines schematically indicate one position of the arm 26 and the dashed lines indicate another possible position into which the arm 26 can be displaced relative to its opposed end 26.1 from the position indicated in solid lines.

It will be understood that the axis 28.2 along which the shaft 28.1 of the instrument 28 extends when mounted on the arm 26 pivots about a pivot center, or fulcrum 50. Thus, irrespective of the movement of the arm 26 relative to its opposed end 26.1, the pivot center 50 normally remains in the same position relative to the stationary cart 20 on which the arm 26 is mounted. In use, the pivot center 50 is positioned at a port of entry into a patient's body when an internal surgical procedure is to be performed. It will be appreciated that the shaft 28.1 then extends through such a port of entry, the wrist-like mechanism 32 being positioned inside the patient's body. Thus, the general position of the mechanism 32 relative to the surgical site in a patient's body can be changed by movement of the arm 26 relative to its opposed end 26.1. Since the pivot center 50 is coincident with the port of entry, such movement of the arm does not excessively effect the surrounding tissue at the port of entry.

As can best be seen with reference to FIG. 4, the arm 26 provides three degrees of freedom of movement to the surgical instrument 28 when mounted thereon. These degrees of freedom of movement are firstly the gimbaled motion indicated by arrows A, pivoting or pitching movement as indicated by arrows B and the linear displacement in the direction of arrows P. Movement of the arm 26 as indicated by arrows A, B and P is controlled by appropriately positioned actuators, e.g., electrical motors, or the like, which respond to actuator command signals, generated in response to inputs from an associated master control, thereby to drive the arm 26 to a required position as dictated by movement of the master control. Appropriately positioned sensors, e.g., potentiometers, encoders, or the like, are provided on the arm 26 to enable a control system of the system 10 to determine the location of the end effector relative to the opposed end 26.1 of the arm 26, in use. The sensors are typically associated with the various pivotal connections of the arm 26 to sense angular positions of the various arm portions of the arm 26 about its pivotal connections. It will be appreciated that whenever "sensors" are referred to in this specification, the term is to be interpreted widely to include any appropriate sensors, such as, for example, positional sensors, velocity sensors, or the like. By causing the arm 26 selectively to displace from one position to another, the general position of the end effector relative to the surgical site can be varied during the performance of the surgical procedure.

Figure 5:
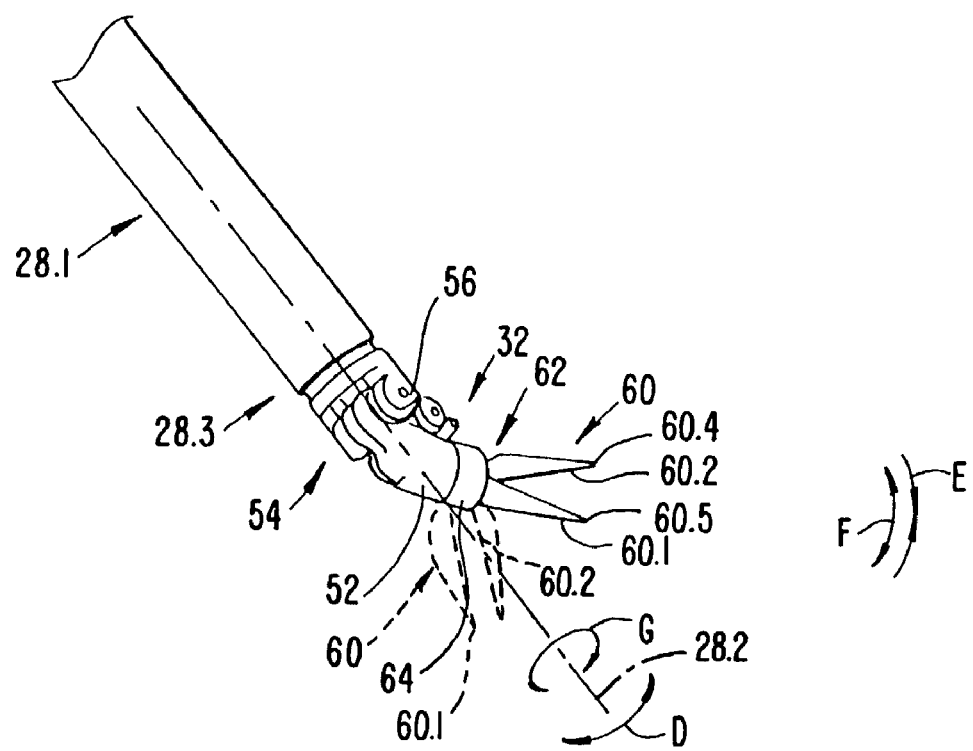
FIG. 5 shows, at an enlarged scale, a wrist member and an end effector of the surgical instrument shown in FIG. 3, the wrist member and the end effector being movably mounted on a working end of a shaft of the surgical instrument.

Referring now to FIG. 5 of the drawings, the wrist-like mechanism 32 will now be described in greater detail. In FIG. 5, the working end of the shaft 28.1 is indicated at 28.3. The wrist-like mechanism 32 includes a wrist member 52. One end portion of the wrist member 52 is pivotally mounted in a clevis, generally indicated at 54, on the end 28.3 of the shaft 28.1 by means of a pivotal connection 56. The wrist member 52 can pivot in the direction of arrows D about the pivotal connection 56. The end effector, generally indicated by reference numeral 60, is pivotally mounted on an opposed end of the wrist member 52. The end effector 60 is in the form of, e.g., a clip applier for anchoring clips during a surgical procedure, or the like. Accordingly, the end effector 60 has two parts 60.1, 60.2 together defining a jaw-like arrangement.

It will be appreciated that the end effector 60 can be in the form of any desired surgical tool, e.g., having two members, or fingers, which pivot relative to each other, such as, for example, scissors, pliers for use as needle drivers, or the like. Alternatively, end effector 60 can include a single working member, e.g., a scalpel, cautery electrode, or the like. When a tool other than a clip applier is required during the surgical procedure, the tool 28 is simply removed from its associated arm 26 and replaced with an instrument bearing the required end effector, e.g., a scissors, or pliers, or the like.

The end effector 60 is pivotally mounted in a clevis, generally indicated by reference numeral 62, on an opposed end of the wrist member 52, by means of a pivotal connection 64. Free ends 60.3, 60.4 of the parts 60.1, 60.2 are angularly displaceable about the pivotal connection 64 toward and away from each other as indicated by arrows E, F. Members 60.1, 60.2 can also be displaced angularly about the pivotal connection 64 to change the orientation of the end effector 60 as a whole, relative to the wrist member 52. Thus, each part 60.1, 60.2 is angularly displaceable about the pivotal connection 64 independently of the other, so that the end effector 60, as a whole, is angularly displaceable about the pivotal connection 64 as indicated in dashed lines in FIG. 5. Furthermore, the shaft 28.1 is rotatably mounted on the housing 34 for rotation as indicated by the arrows G. Thus, the end effector 60 has three degrees of freedom of movement relative to the arm 26, namely, rotation about the axis 28.2 as indicated by arrows G, angular displacement as a whole about the pivot 64 and angular displacement about the pivot 56 as indicated by arrows D. By moving the end effector 60 within its three degrees of freedom of movement, its orientation relative to the end 28.3 of the shaft 28.1, and, accordingly, also relative to the opposed end 26.1 of the arm 26, can selectively be varied.

It will be appreciated that movement of the end effector 60 relative to the end 28.3 of the shaft 28.1 is controlled by appropriately positioned actuators, e.g., electrical motors, or the like, which respond to actuator command signals generated by the control system in response to inputs from the associated master control, thereby to cause the actuators to drive the end effector 60 to a required orientation as dictated by movement of the master control. Furthermore, appropriately positioned sensors, e.g., encoders, or potentiometers, or the like, are provided to permit the control system of the system 10 to determine angular positions of the wrist member 52 relative to the shaft 28.1 and of the end effector 60 relative to the wrist member 52.

One of the master controls is indicated generally by reference numeral 70 in FIG. 6. The master control defines a master arm, generally indicated by reference numeral 71. A hand-grippable part, in the form of a pincher formation indicated at 86, is mounted on one end 71.2 of the master arm 71. An opposed end 71.1 of the master arm 71 is connected to the surgeon's console 12. The hand-grippable part is movable relative to the opposed end 71.1 of the master arm 71. The master arm 71 includes a wrist gimbal 80 on which the hand-grippable part is mounted. The master arm further includes an arm portion 90. The gimbal 80 has a plurality of arm portions 82 connected one to another by means of pivotal connections, or joints, 84. In use, the surgeon grips the hand-grippable part 86 by positioning his or her thumb and index finger over opposed fingers of the part 86. When the fingers are squeezed between the thumb and index finger, the end effector elements 60.1, 60.2 of the end effector 60 close. When the thumb and index finger are moved apart, the elements 60.1, 60.2 of the end effector 60 move apart in sympathy with the moving apart of the fingers of the part 86. The pivotal connections 84 of the gimbal 80 are operatively connected to actuators, e.g., electric motors, or the like, to provide for, e.g., force feedback, gravity compensation, and/or the like. Furthermore, appropriately positioned sensors, e.g., encoders, or potentiometers, or the like, are associated with each pivotal connection 84 of the gimbal 80, so as to enable angular positions of the arm portions 82 of the gimbal 80 about its pivotal connections to be determined by the control system of the system 10.

The arm portion 90 includes a plurality of arm portions or links 92 connected one to another by means of pivotal connections, or joints, 94. It will be appreciated that actuators e.g., electric motors, or the like, are also associated with the arm portion 90, to provide for, e.g., force feedback, gravity compensation, and/or the like. Furthermore, sensors, e.g., encoders, or potentiometers, or the like, are operatively associated with the pivotal connections 94 so as to enable angular positions of the arm portions 92 of the arm portion 90 about its pivotal connections to be determined by the control system.

To cause the end effector 60 to move relative to the opposed end 26.1 of the arm 26, the surgeon simply moves the hand-grippable part 86 relative to the opposed end 71.1 of the master arm thereby to cause the end effector 60 to move relative to the opposed end 26.1 of the instrument arm 26 on which it is mounted and to where the surgeon wants the end effector 60 to be with reference to the image displayed on the image display 14. Thus, the end effector position and/or orientation is typically caused to follow that of the hand-grippable part 86.

The actuators and sensors associated with the arms 26, 26 and the surgical instruments 28, 28 mounted thereon, and the actuators and sensors associated with the master controls 70, 70 are operatively linked in the control system. The control system typically includes at least one processor, typically a plurality of processors, for effecting control between master control device input and responsive end effector movement output and for effecting control between end effector input and responsive master control output in the case of, e.g., force feedback, or the like.

Figure 7:
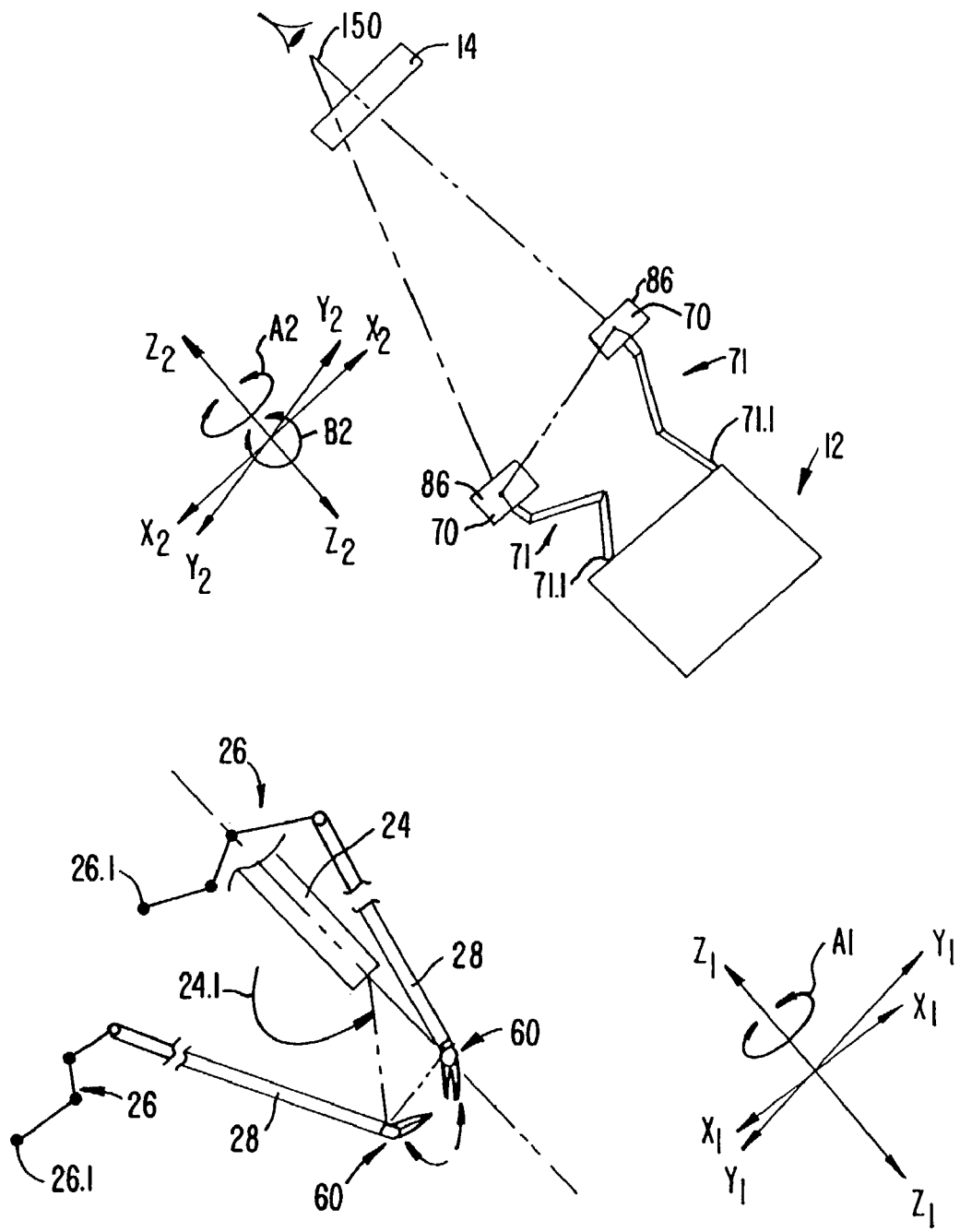
FIG. 7 shows a schematic three-dimensional drawing indicating the positions of the end effectors relative to a viewing end of an endoscope on the surgical station and the corresponding positions of the master control devices relative to the eyes of an operator, typically a surgeon, at the control station.

In use, and as schematically indicated in FIG. 7 of the drawings, the surgeon views an image of the surgical site on the image display 14. The end effector 60 carried on each arm 26 is caused to perform locational movements, in the form of positional and orientational movements, relative to the opposed ends 26.1, 26.1 of the arms 26, 26 in response to locational movements, in the form of orientational and positional movements, of the hand-grippable parts 86, 86 relative to the opposed ends 71.1, 71.1 of the master arms 71, 71. The master controls are indicated schematically at 70, 70. It will be appreciated that during a surgical procedure images of the end effectors 60, 60 are captured by the endoscope 24 together with the surgical site and are displayed on the image display 14 so that the surgeon can view responsive movements of the end effectors 60, 60 as he or she controls such movements by means of the master controls 70, 70. The control system is arranged automatically to cause end effector orientational and positional movement relative to the opposed ends 26.1, 26.1 of the arms 26, 26 to correspond with orientational and positional movement of the hand-grippable parts 86, 86 relative to the opposed ends 71.1, 71.1 of the master arms 71, 71 in terms of a predetermined positional and/or orientational relationship as will be described in greater detail herein below.

The operation of the control system of the system 10 will now be described. In the description which follows, the control system will be described with reference to a single master control 70 and its associated instrument arm 26 and end effector 60. As will be understood by those of skill in the art of robotics, the control system will generally comprise a computer program of machine-readable code embodying instructions for performing the methods described herein. The computer program will often comprise a tangible media such as magnetic recording media (often in the form of a hard disk or floppy disk), optical recording media (such as an optical compact disk or digital video disk), or the like and may be embodied as hardware, firmware, software, or the like. In some embodiments, the program may be transmitted to the control system processor by an input system such as an internet, an intranet, an Ethernet, an input/output port, or the like.

Figure 8:
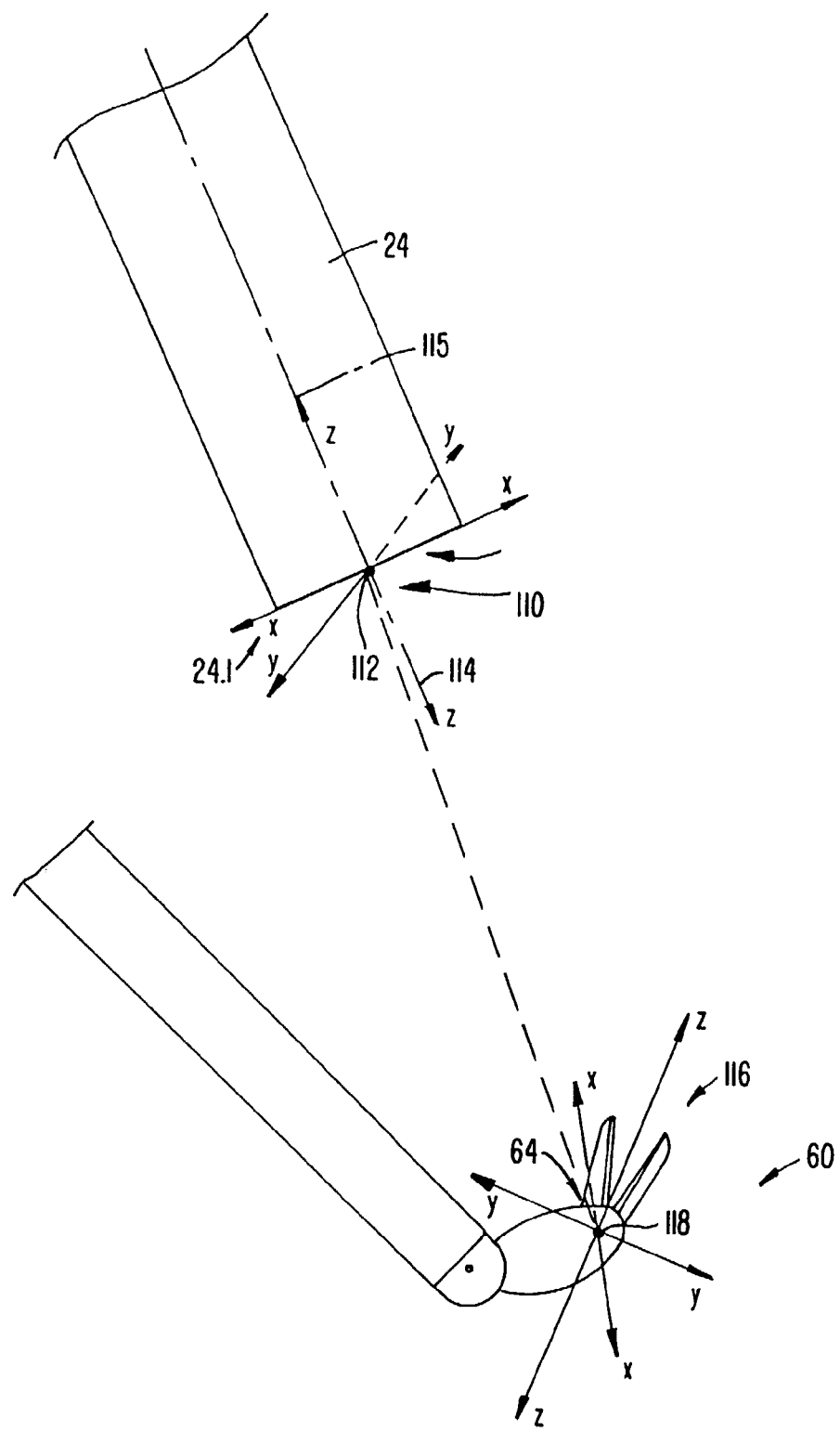
FIG. 8 shows a schematic three-dimensional drawing indicating the position and orientation of an end effector relative to a camera Cartesian coordinate reference system at a viewing end of the endoscope.

The method whereby control between hand-grippable part movement and corresponding end effector movement is achieved by the control system of the system 10 will now be described with reference to FIGS. 8 to 10 of the drawings in overview fashion. For a more detailed description of such control, refer to Applicant's co-pending U.S. patent application Ser. No. 09/373,678, entitled "Camera Referenced Control in a Minimally Invasive Surgical Apparatus," filed Aug. 13, 1999, which is fully incorporated herein by reference as if part of this specification.

Control between hand-grippable part and end effector movement is achieved by comparing hand-grippable part position and orientation relative to an eye Cartesian coordinate reference system with end effector position and orientation relative to a camera Cartesian coordinate reference system. For ease of understanding and economy of words, the term "Cartesian coordinate reference system" will simply be referred to as "frame" in the rest of this specification. Accordingly, when the hand-grippable part is stationary, the end effector position and orientation relative to the camera frame is compared with the hand-grippable part position and orientation relative to the eye frame, and should the position and/or orientation of the end effector relative to the camera frame not correspond with the position and/or orientation of the hand-grippable part relative to the eye frame, the end effector is urged to move into a position and/or orientation relative to the camera frame at which its position and/or orientation relative to the camera frame would correspond with the position and/or orientation of the hand-grippable part relative to the eye frame. In FIG. 8, the camera frame is generally indicated by reference numeral 110 and the eye frame is generally indicated by reference numeral 150 in FIG. 9.

When the hand-grippable part 86 is moved into a new position and/or orientation relative to the eye frame 150, the new position and/or orientation does not correspond with the previously corresponding position and/or orientation of the end effector relative to the camera frame 110. The control system then causes the end effector to be urged to move into a new position and/or orientation relative to the camera frame 110 at which new position and/or orientation its position and orientation relative to the camera frame 110 would correspond with the new position and/or orientation of the hand-grippable part relative to the eye frame 150.

It will be appreciated that the control system includes at least one processor which is arranged to compute new corresponding positions and/or orientations of the end effector in response to hand-grippable part movement on a continual basis at a rate corresponding to the processing cycle rate of the control system. A typical processing cycle rate of the control system is about 1300 Hz or more. Thus, when the hand-grippable part is moved from one position and/or orientation to a next position and/or orientation, the corresponding movement of the end effector to respond is computed at at least about 1300 Hz. Naturally, the control system can have any appropriate processing cycle rate depending on the processor, or processors, used in the control system.

The camera frame 110 is typically positioned such that its origin 112 is at the viewing end 24.1 of the endoscope 24. Conveniently, the z axis of the camera frame 110 extends axially along a viewing axis 114 of the endoscope 24. Although, in FIG. 8, the viewing axis 114 is shown in coaxial alignment with a shaft axis 115 of the endoscope 24, it is to be appreciated that the viewing axis 114 can be angled relative thereto. Thus, the endoscope can be in the form of an angled scope. Naturally, the x and y axes are positioned in a plane perpendicular to the z axis. The endoscope is typically angularly displaceable about its shaft axis. The x, y and z axes are fixed relative to the viewing axis 114 of the endoscope 24 so as to displace angularly about the shaft axis in sympathy with angular displacement of the endoscope 24 about its shaft axis 115.

To enable the control system to determine end effector position and orientation, a frame is defined on, or attached relative to, the end effector 60. This frame is referred to as an end effector frame, or slave tip frame, in the rest of this specification, and is generally indicated by reference numeral 116. Conveniently, the end effector frame 116 has its origin at the pivotal connection 64. However, depending on the type of end effector used, the origin may be offset relative to such a pivotal connection should an improved or more intuitive response between hand-grippable part movement input and end effector movement output be achieved thereby. For the end effector 60 as shown in the drawings, one of the axes, e.g., the z axis of the frame 116, is defined to extend along an axis of symmetry, or the like, of the end effector 60. Naturally, the x and y axes then extend perpendicularly to the z axis. It will be appreciated that the orientation of the end effector is then defined by the orientation of the frame 116 having its origin at the pivotal connection 64, relative to the camera frame 110. Similarly, the position of the end effector is then defined by the position of the origin 118 of the frame 116 relative to the camera frame 110.

Figure 9:
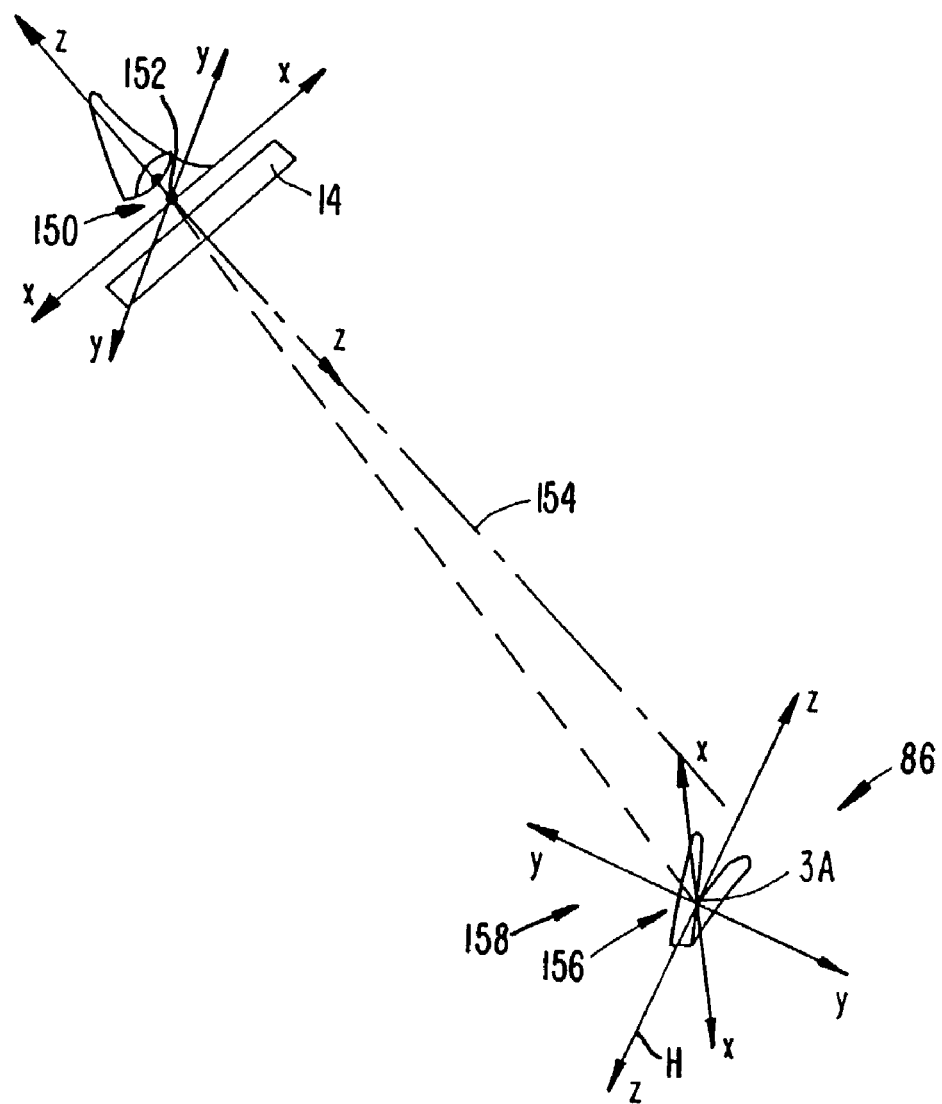
FIG. 9 shows a schematic three-dimensional drawing indicating the position and orientation of a hand-grippable part or pincher formation, of one of the master control devices, relative to an eye Cartesian coordinate reference system at an image display or viewer of the control station.

Referring now to FIG. 9 of the drawings, the eye frame 150 is typically chosen such that its origin corresponds with a position 152 where the surgeon's eyes are normally located when he or she is viewing the image of the surgical site displayed on the image display 14. The z axis typically extends along a line of sight of the surgeon, indicated by axis 154, when viewing the image on the image display 14. Naturally, the x and y axes then extend perpendicularly from the z axis at the origin 152. Conveniently, the y axis is chosen to extend generally vertically relative to the image display 14 and the x axis is chosen to extend generally horizontally relative to the image display 14.

To enable the control system to determine hand-grippable part position and orientation in the eye frame 150, an appropriate point, e.g., point 3A, is chosen on the hand-grippable part to define an origin 156 of a master frame 158. It will be appreciated that the point relative to the hand-grippable part at which the origin 156 of the master frame 158 is attached is chosen to enhance intuitive response between hand-grippable part movement input and responsive end effector movement output and can thus be at any appropriate location relative to the hand-grippable part. Conveniently, the z axis of the master frame 158 extends along an axis of symmetry of the hand-grippable part 86 which extends coaxially along a rotational axis H of the hand-grippable part 86. The x and y axes then extend perpendicularly from the rotational axis H at the origin 3A. Accordingly, orientation of the hand-grippable part relative to the eye frame 150 is defined by the orientation of the master frame 158 relative to the eye frame 150. The position of the hand-grippable part relative to the eye frame 150 is defined by the position of the origin 156 at 3A relative to the eye frame 150.

Figure 10:
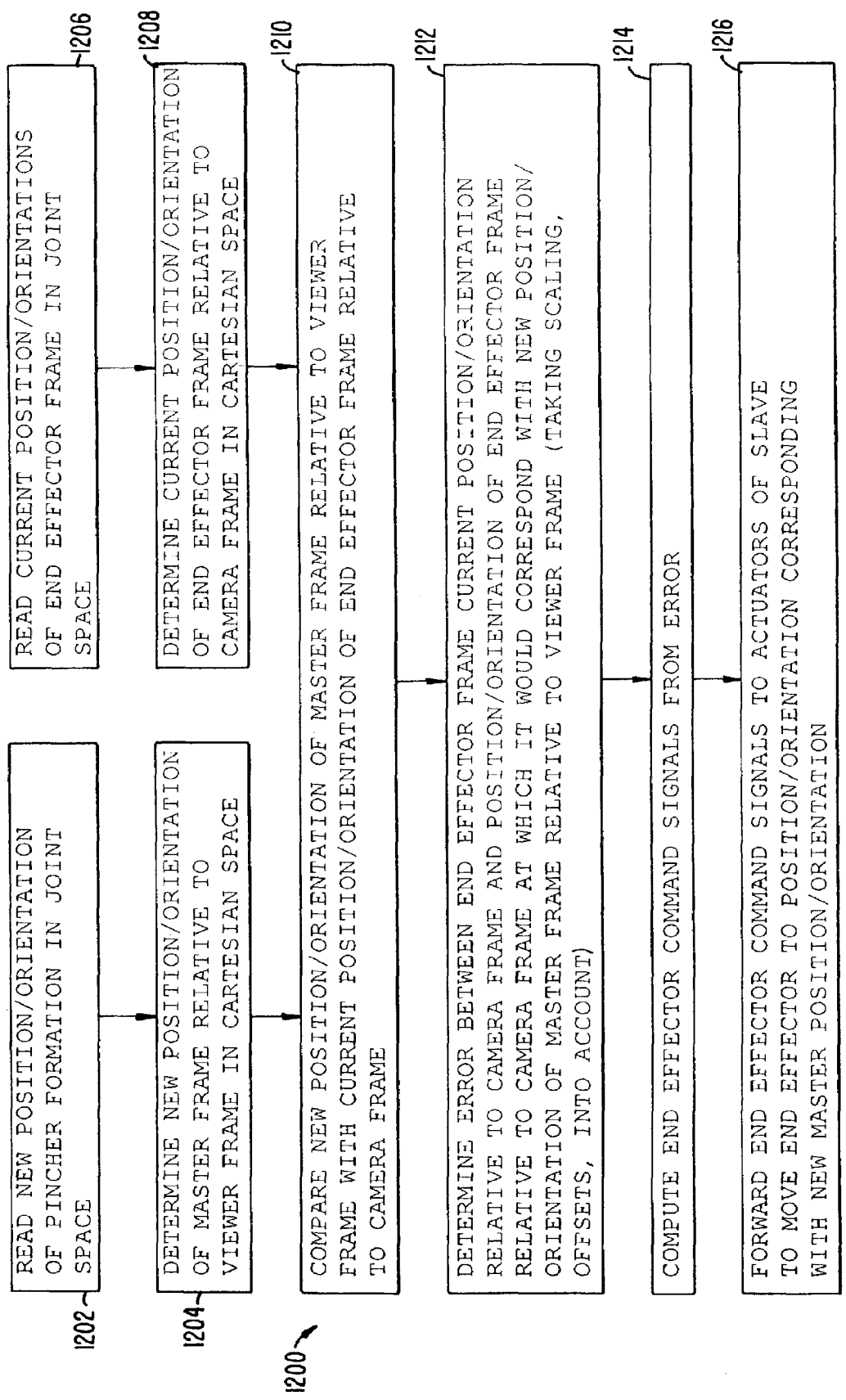
FIG. 10 shows a block diagram indicating control steps of a control system of the surgical system, the control system being arranged to effect control between master control device input and corresponding surgical instrument movement output.

Referring now to FIG. 10 of the drawings, a block diagram corresponding to part of the control system which is employed to cause the end-effector to move in response to movement of the hand-grippable part, is generally indicated by reference numeral 1200. As a starting point, for ease of description, it is assumed that the hand-grippable part and the end effector were at corresponding positions and orientations and that the hand-grippable part has been moved into a new position and/or orientation. Accordingly, since the new position and/or orientation of the hand-grippable part 86, and consequently that of the master frame 158, relative to the eye frame 150, no longer corresponds with the position and/or orientation of the end effector frame 116 relative to the camera frame 110, the end effector 60 is urged to move into a new position and/or orientation such that the position and/or orientation of the end effector frame 116 relative to the camera frame 110 would correspond with the new position and/or orientation of the master frame 158 relative to the eye frame 150.

The new position and/or orientation of the hand-grippable part 86 is read in "joint" space as indicated by reference numeral 1202. This is achieved by the processor by means of the sensors operatively associated with the master arm 71. From this joint space information, which determines the angular positions of the arm portions of the master arm about its pivotal connections, a corresponding new position and/or orientation of the master frame 158 relative to the eye frame 150 is determined in Cartesian space as indicated by reference numeral 1204. In similar fashion, the current position and orientation of the end effector 60 in joint space is read as indicated by reference numeral 1206. From this information the current position and orientation of the end effector frame 116 relative to the camera frame 110 in Cartesian space is computed, as indicated by reference numeral 1208. The new position and/or orientation of the master frame 158 relative to the eye frame 150 in Cartesian space is then compared with the current position and orientation of the end effector frame 116 relative to the camera frame 110 as indicated at 1210. An error between the end effector frame 116 current position and orientation relative to the camera frame 110 and the position and/or orientation of the end effector frame 116 relative to the camera frame 110 at which it would correspond with the new position and/or orientation of the master frame 158 relative to the eye frame 150 is then computed, as indicated at 1212.

It will be appreciated that the hand-grippable part orientational and positional movement need not necessarily correspond proportionally with responsive end effector orientational and positional movement. The system is typically arranged to provide for scaling so that the translational movement of the end effector in response to translational movement input on the hand-grippable part can be scaled e.g., at a ratio 1 to 2, or the like. Accordingly, the positional and orientational input on the hand-grippable part can be converted into corresponding positional and orientational movement output of the end effector in terms of a predetermined locational relationship between hand-grippable positional and orientational movement input relative to the opposed end 71.1 of its associated master arm 71 and responsive end effector positional and orientational movement output relative to the opposed end 26.1 of its associated instrument arm 26.

From the error, corresponding end effector actuator command signals are generated or computed as indicated at 1214. The end effector actuator command signals are then communicated to the actuators associated with the end effector to cause them to drive the end effector 60 into a new position and/or orientation so that the end effector frame 116 relative to the camera frame 110 is correspondingly moved into a new position and/or orientation relative to the camera frame 110 at which it corresponds with the new master frame position and/or orientation relative to the eye frame 150, as indicated at 1216. For further detail regarding such end effector command signals, refer to U.S. patent application Ser. No. 09/373,678, as mentioned above.

In the course of the surgical procedure, the surgeon may wish to change the image of the surgical site displayed on the image display 14. It is an object of this invention to provide methods and systems by which this can be achieved. This will now be described.

Figure 11:
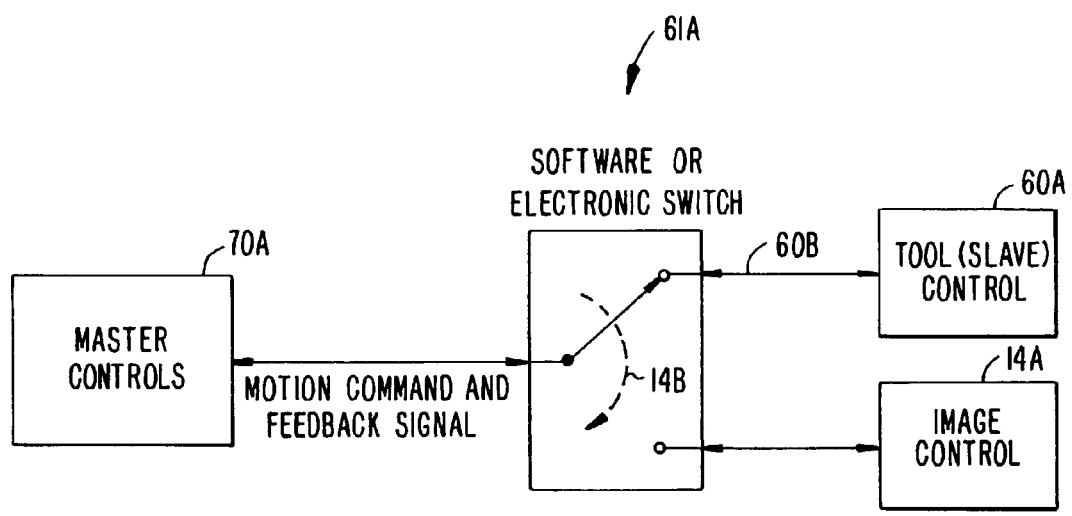
FIG. 11 shows a schematic view of switching of operative association from between one, or both, of the master controls and the end effectors to between one, or both, of the masters and the image displayed on the image display.

To do this, a suitable selection input (not shown) is actuated, typically at the control console 12. Such a suitable input can typically include a depressable foot pedal, typically located at the console 12. Instead, the selection input can include a voice actuatable input, or a pressable button, or the like, located at the console 12, or on one of the master controls 70, 70. When the selection input is actuated, the control system switches operative association from between the master controls 70, 70 and the arms 26, 26 and instruments 28, 28 to between one, or both, of the master controls 70, 70 and the image displayed on the image display 14. This is shown in FIG. 11 of the drawings. In FIG. 11, the master controls are indicated schematically at 70A. Part of the selection input is schematically indicated at 61A. Operative association between the arms 26, 26 and their associated end effectors 60, 60 is indicated schematically at 60A and operative association with the displayed image is indicated at 14A. Upon actuation of the selection input 61A, operative association is changed from between the master controls 70A and the arms 26, 26 and end effectors 60, 60, to between the master controls 70A and the displayed image, as indicated by the dashed arrow 14B. The part of the selection input 61A can include a software or electronic switch associated with the foot pedal, button, voice actuator, or the like.

One, or both, master controls can then be used to cause the displayed image to change. Changing the displayed image can be achieved by regulating regulatable information, such as digital information, associated with the captured image, as described in greater detail herein below, and/or by causing the endoscope to move relative to the surgical site. After the image has been changed, operative association between the master controls and the end effectors is restored.

Upon actuation of the selection input, operative association between the master controls 70, 70 and the end effectors 60, 60 is interrupted. Upon such interruption, the end effectors 60, 60 are typically locked in the positions and orientations that they were in immediately prior to actuation of the selection input. Accordingly, the end effector positions and orientations are locked relative to the cart 20. Since the cart 20 is normally stationary relative to the patient in use, the end effectors 60, 60 are consequently also retained in stationary positions and orientations relative to the patient. The control system achieves this by locking the end effector frames 116, 116 in position and orientation relative to a world reference frame attached relative to the cart 20.

In this specification, the term "world reference frame" is to be interpreted to mean suitable reference frames, such as Cartesian reference frames, which are used by the control system to determine positions and orientations of the end effector frames 116, 116, the master frames 158, 158, and the camera frame 110 in the end effector workspace or master controller workspace. It will be appreciated that such world reference frames can be attached relative to any appropriate part of the surgeon's console 12 and the cart 20 respectively. By way of example, a world reference frame may be attached to the surgeon's console at the viewer 14, as can best be seen with reference to FIG. 1 and as indicated at 14B.

In use, the control system determines the positions and orientations of the hand-grippable parts 86, 86 relative to the opposed ends 71.1, 71.1 of the master arms 71, 71 by determining the positions and orientations of the master frames 158, 158 relative to the world frame 14B. In system 10, the world frame 14B is chosen to correspond with the eye frame 150. In similar fashion, and with reference to FIG. 1, a world reference frame is attached to the cart 20 as indicated schematically at 14C. The world reference frame 14C is attached to the cart so that the positions and orientations of the end effectors 60, 60 and the orientation and position of the endoscope 24, relative to the opposed ends 26.1, 26.1 and 22.1 of the arms 26, 26 and 22 can be determined by determining the positions and orientations of the end effector frames 116, 116 and the camera frame 110 relative to the world frame 14C.

Upon actuation of the selection input, the master controls 70, 70 are freed from the end effectors and can then be used for purposes other than causing end effector movement in response to movement of the hand-grippable parts 86, 86 relative to the opposed ends 71.1, 71.1 of the master arms 71, 71.

One, or both, master controls 70, 70 can then be used to cause the image displayed on the image display 14 to change in response to movement of one, or both, hand-grippable parts 86, 86 relative to the opposed ends 71.1, 71.1 of the master arms 71, 71.

In one preferred embodiment, one, or both, master controls 70, 70 are used to change the displayed image by causing the endoscope 24 to move relative to the opposed end 22.1 of its associated arm 22, thereby, in use, to cause the viewing end 24.1 of the endoscope 24 to change in position and/or orientation relative to the surgical site so as to change the image of the surgical site displayed on the image display 14.

The camera arm 22 is arranged to move the endoscope 24 relative to its opposed end 22.1 typically in four degrees of freedom of movement. These degrees of freedom of movement are indicated schematically in FIG. 12 of the drawings. The degrees of freedom of movement are rotation about the longitudinal axis 115 of the endoscope 24, as indicated by the arrow A1, translation in a direction extending along the longitudinal axis 115 as indicated by arrow A2, and pivotal movement relative to a pivot point or fulcrum 50B, as indicated by arrows A3 and A4. The camera arm 22 is similar to the arms 26, 26 in that the arm 22 defines a fulcrum 50B, about which the endoscope 24 is constrained to move or pivot. It will be appreciated that the camera arm 22 has arm portions connected one to another by means of pivotal connections, that sensors are associated with the camera arm 22 to enable the control system to determine the position and orientation of the endoscope 24 relative to the opposed end 22.1 of the arm 22, and actuators associated with the camera arm 22 for driving the endoscope 24 to displace relative to the end 22.1 of the arm 22 within the four degrees of freedom of movement of the endoscope 24.

As mentioned, and as can best be seen with reference to FIG. 1, the control system defines a world reference frame attached relative to the ends 22.1, 26.1, 26.1 of the arms 22, 26, 26 respectively, as indicated at 14C. Since the ends 22.1, 26.1, 26.1 are connected to the cart 20, the world reference frame 14C is attached relative to the cart 20 so that the positions and orientations of the end effector frames 158, 158 and the camera frame 110 can readily be determined with reference to the world frame 14C.

One preferred method whereby the displayed image on the image display 14 can be changed by means of the master controls 70, 70 includes using both hand-grippable parts 86, 86 together, to change the position and/or orientation of the endoscope 24 relative to the opposed end 22.1 of the camera arm 22. This method will now be described with reference to FIG. 13.

Figure 13A:
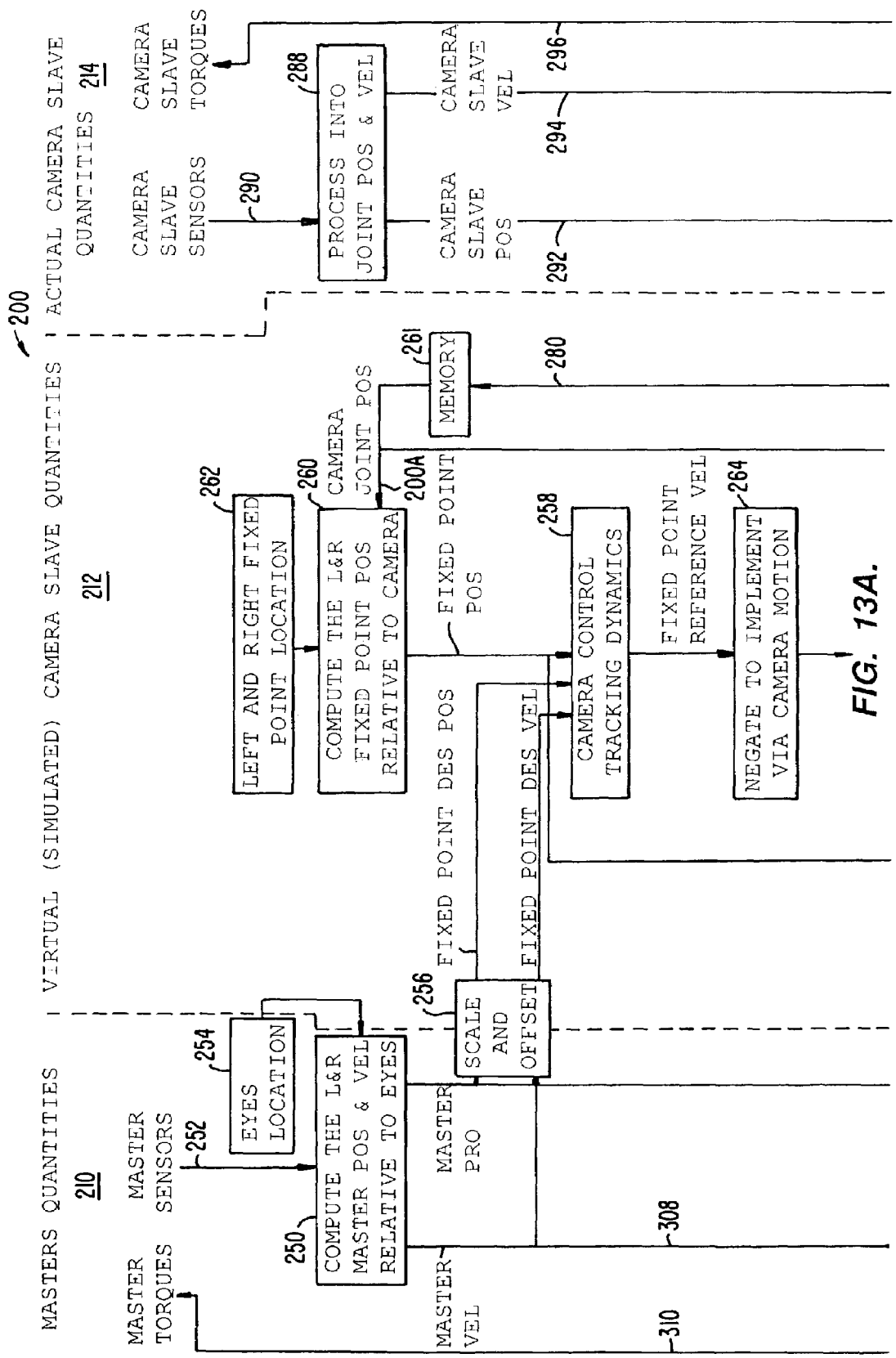
FIG. 13 shows an algorithm indicating steps employed in a control system for performing an image change in accordance with the invention.
Figure 13B:
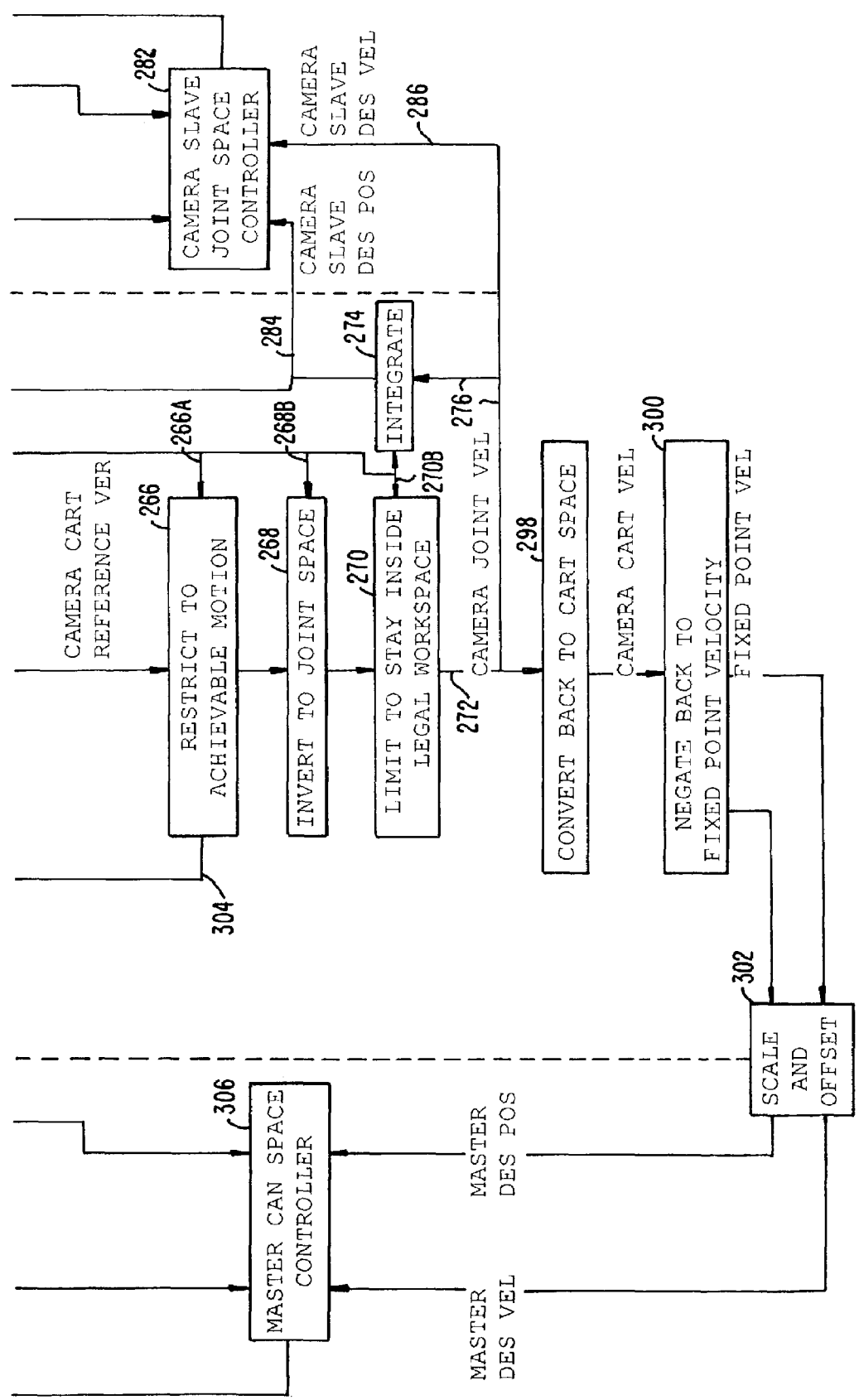

In FIG. 13, an algorithm 200 is indicated. The algorithm 200 is representative of the control system employed to achieve the image shift as described above.

The algorithm 200 can be divided into 3 portions for ease of understanding. The part of the algorithm indicated by reference numeral 210 represents a master control portion or master quantities. Reference numeral 212 indicates a computational control process portion or virtual (simulated) camera slave quantities, and reference numeral 214 indicates a slave portion or actual camera slave quantities. It is to be appreciated that the term camera applies to the endoscope 112.

As mentioned, upon activation of the foot pedal, the control system as exemplified by the algorithm 200 is initialized. The position of the master controls 70, 70 relative to each other is then locked. However, the master controls 70, 70 are still free to move in the Cartesian space relative to the viewer 14. As the surgeon then moves the master controls 70, 70 to, e.g., shift the image, information corresponding to the positions and velocities of the master controls 70, 70 is received at 250. This information is derived from the appropriately positioned sensors, e.g., encoders, potentiometers, or the like, (not shown), operatively associated with the master controls 70, 70 as indicated at 252. Appropriate sensors are positioned at the viewer 14 to register the presence of the surgeon looking at the viewer 14. It will be appreciated that the sensors at the viewer 14 correspond to a fixed spatial point of reference, as indicated by reference numeral 254. At 250 the fixed point reading or input from 254 is compared with the position and velocity readings or inputs from 252, and a fixed point position and velocity of each master control 70, 70 is calculated relative to the fixed point. In FIG. 9, the fixed point is indicated at 152, the fixed point position and velocity of each master control 70, 70 being indicated at 156, 156, respectively. It will be appreciated that the fixed points 152, 156, 156 need not necessarily be at the specific positions indicated.

The fixed point position and velocity of the master controls 70, 70 is then scaled and offset at 256. It will be appreciated that the actual distances between each master control 70, 70 and the viewer 14 does not correspond to the actual distances between each end effector 60, 60 and the end 24.1 of the endoscope 24. Therefore, scaling is required. Furthermore, the positions of the master controls 70, 70 relative to the viewer 14, and relative to each other, would likely not correspond with the positions of the end effectors 60, 60 relative to the end 24.1 of the endoscope 24 and relative to each other.

Accordingly, after the scaling and offsetting step at 256, a scaled and offset position and velocity of each master control 70, 70 is obtained. This information is then passed to 258.

At 260, the fixed point position of each end effector 60, 60 relative to the end of the endoscope 24 is calculated. Again, it is to be appreciated that the fixed points need not necessarily be positioned where indicated. This is advantageously achieved by means of a positional input corresponding to the location of the end effectors 60, 60. It will be appreciated that since use is being made of reference frames, this procedure could function without the surgical instruments being mounted on the arms 26, 26. This input is derived from the appropriate sensors (not shown) operatively associated with the end effectors 60, 60. This positional input is compared with a camera position input obtained from memory 261, to calculate the position of each end effector 60, 60 relative to the endoscope 24. This could be obtained from real position information instead of "virtual/simulated" information as herein described.

It will be appreciated that at 258 the velocity of the end effectors 60, 60 to "catch up" to the position and velocities of the scaled and offset positions and velocities of the master controls 70, 70 was determined. Bearing in mind that the end effectors 60, 60 are stationary and we are dealing with relative positions, a resultant velocity of the camera is determined in relation to the stationary end effectors 60, 60 at 264. This resultant velocity corresponds to the velocities of the end effectors 60, 60 had the camera been stationary.

The fixed point positions of each end effector 60, 60 is then also passed to 258. At 258 the fixed point position of each end effector 60, 60 relative to the endoscope 24 is compared with the fixed point scaled and offset positions and velocity of each master control 70, 70. At 258 a fixed point reference velocity for each end effector 60, 60 is calculated. It will be appreciated that the fixed point reference velocity corresponds to the velocities that are required by the end effectors 60, 60 to "catch up" to the scaled and offset positions and velocities of each master control 70, 70. These fixed point reference velocities are then passed to 264. At 264 the fixed point reference velocities are converted to a required camera velocity, since the end effectors 60, 60 are stationary. The reference velocity computed at 264 forms an input to 266.

With reference to FIG. 7, and in particular to the associated accompanying coordinate diagrams, the end of the endoscope 24 is typically able to rotate as indicated at A1 and is able to move in x-y and z directions indicated by X1, Y1 and Z1. Thus, the endoscope 24 has four degrees of freedom of movement. The master controls 70, 70 typically have more than four degrees of freedom of movement. The master controls 70, 70 can advantageously, though not necessarily, have freedoms of movement corresponding to those of the end effectors 60, 60 as indicated by A2, X2, Y2 and Z2, in the associated coordinate diagram in FIG. 7.

If the camera reference velocity has a velocity component falling beyond the possible freedoms of movement of the endoscope 24, e.g., a rotational component about the X2-X2 axis as indicated by B2 in FIG. 7, this component is rejected at 266. Thus, the camera reference velocity is restricted to fall within the movements mechanically possible by the endoscope 24.

The camera reference velocity, after having been restricted to achievable camera motion at 266, then forms an input to 268. At 268 the camera reference velocity is converted to servo motor instructions. The endoscope 24 can be driven by servo motors (not shown) arranged to displace the end of the endoscope 24 within its available degrees of freedom of movement. Thus, the servo motor instructions are such as to provide the camera reference velocity to the end 24.1 of the endoscope 24.

It will be appreciated that the endoscope 24 often has a limited range of movement within each of its four degrees of freedom of movement. Thus, if the servo motor instructions are such that if performed it would fall beyond the bounds of the mechanically possible range of movement, the instructions need to be limited so that the actual servo motor movement falls within its possible range. Thus, at 270, the servo motor instruction is limited to remain within the possible range of movement if the instruction is such that a motion beyond the possible range of any one of the four degrees of freedom of movement is instructed. Similarly, as the field of view of endoscope 24 is often known, the control system may inhibit motion of the scope which would result in one or more tools being disposed outside the field of view of the endoscope (and hence beyond the image shown to the system operator).

Thus, the output from 270, namely 272, forms a servo motor instruction in the form of a camera joint velocity or a desired camera slave velocity. This output 272 forms an input to 274 via branch 276. At 274, the camera joint velocity is integrated to obtain a camera joint position or desired camera slave or servo motor position at 280.

The output 272 forms an input to the memory 261 via branch 280 so as to update the memory 261 with a new camera joint position. It will be appreciated that the memory keeps track of the position and feeds this information to 266, 268, and 270.

It will be appreciated that during an image shift the control system path defined from 258 to 264, from 264 to 266, from 266 to 268, from 268 to 270, from 270 to 274, from 274 to 261, from 261 to 260 and from 260 back to 258 is followed cyclically, typically at a rate of 1300 times per second, and, is constantly adapting to new inputs from 256 and 250 in response to master control 70, 70 movement and changes in position of the end effectors 60, 60 relative to the camera or endoscope 24.

The output 280 forms an input to 282 via branch 284. Similarly, the output 272 forms also an input to 282 via branch 286.

At 288 joint position and velocity is calculated via inputs from camera slave sensors (not shown) indicated by reference numeral 290. The actual camera slave position and velocity forms inputs to 282 via branches 292 and 294, respectively. At 282, a camera slave joint space controller, the actual camera slave position and velocity inputs 292, 294 are compared with the required camera slave position and velocity inputs from 284 and 286 to yield a resultant torque which is communicated to the camera slave motors via branch 296.

The camera joint velocity output 272 from 270 forms an input to 298 also. At 298 the camera joint velocity is converted back to a camera or endoscope velocity. The camera velocity thus obtained forms an input to 300.

At 300 the camera velocity is transferred back to a fixed point velocity at the end effectors 60, 60. These fixed point velocities form inputs to 302. The fixed point position of the end effectors 60, 60 also forms an input to 302 from 260 via branch 304. At 302 the fixed point positions and velocities of the end effectors 60, 60 are scaled and offset to positions and velocities corresponding to the master controls 70, 70.

At 306, a master Cartesian space controller, the master desired position and velocity is received from 302 as an input, and the actual master control 70, 70 position and velocity is received from 250 via branches 308 and 310, respectively. The information from 302 and that from 250 is compared at 306. In the event that the required position and velocity of the endoscope falls outside the constraints at 266, 268 or 270, appropriate torque is transmitted to master control servo motors to indicate to the surgeon that the motion input is not possible. Thus, the surgeon feels the bounds of available motion.

Referring again to FIG. 13, the algorithm indicating the control steps used in this preferred method of changing the image displayed on the image display 14 as generally indicated by reference numeral 200, will now be described in an alternative manner.

The algorithm 200 can be divided into three portions for ease of explanation and understanding. Accordingly, the portion of the algorithm 200 indicated at 210 represents master control quantities, the portion 212 indicates a control process portion or virtual (simulated) camera quantities and reference numeral 214 indicates a portion of the algorithm 200 which indicates actual camera quantities. It will be appreciated that the term "camera" refers to the endoscope 24 where used in the specification, and that the invention encompasses manipulation of images provided from other sources including fluoroscopes, ultrasound transducers, MRI systems, and other imaging modalities.

Upon actuation of the selection input, the control system as shown by the algorithm 200 is initialized to cause the endoscope 24 to be moved relative to the opposed end 22.1 of the camera arm 22 in response to movement of the hand-grippable parts 86, 86 relative to the opposed ends 71.1, 71.1 of the master arms 71, 71. Upon interruption of the operative association with the end effectors 60, 60, the end effectors are caused to be locked orientationally and positionally relative to the opposed ends 26.1, 26.1 of the arms 26, 26, as already described. Furthermore, the hand-grippable parts 86, 86 are locked in the positions relative to each other at which they were immediately prior to actuation of the selection input. However, the hand-grippable parts 86, 86 are still free to move relative to the opposed ends 71.1, 71.1 of the master arms 71, 71. The endoscope 24 is then caused to move relative to the opposed end 22.1 of its camera arm 22 in response to moving the hand-grippable parts 86, 86 relative to the ends 77.1, 77.1 while the hand-grippable parts 86, 86 are locked in position relative to each other.

Referring now to the algorithm 200, the positions and velocities of the master frames 158, 158 relative to the world reference frame 14B at the control console 12 is determined at 250. As mentioned, the world reference frame 14B is chosen to be defined by the eye reference frame 150. It is to be appreciated that the world reference frame 14B can be located at any other appropriate position. However, it has been found to be convenient to attach the world reference frame 14B to coincide with the eye reference frame 150.

Determining the position and velocities of the master reference frames 158, 158 relative to the world reference frame 14B is achieved by means of the sensors associated with the master arms 71, 71 sensing the angular positions and velocities of the arm portions of the master arms 71, 71 about their pivotal connections as indicated at 252 and comparing this information with the location of the world reference frame 14B as indicated at 254.

The positions and velocities of the master frames 158, 158 relative to the world frame 14B, or eye frame 150, is then input to 256, a scale and offset step. It is to be appreciated that the control system is preferably manipulating with "Cartesian space" quantities (although other reference frames might also be used). Furthermore, it is to be appreciated that the actual distances between the hand-grippable parts 86, 86 is typically not the same as the actual distances between the end effectors 60, 60. Furthermore, the actual distances between the hand-grippable parts 86, 86 and the world frame 14B is typically not the same as the distances between the end effectors 60, 60 and the camera frame 110. The scale and offset step at 256 is used to transform the positions of the master frames 158, 158 relative to each other, and the positions and velocities of the master frames 158, 158 relative to the world frame 14B into positions and velocities which correspond with the positions of the end effector frames 116, 116 relative to each other and to correspond with the positions of the end effector frames 116, 116 relative to the camera frame 110.

After the scale and offset step at 256, a corresponding scaled and offset position and velocity of each master frame 158, 158 relative to the world frame 14B, or eye frame 150, is forwarded to 258.

At 260, the positions of each end effector frame 116 relative to the camera frame 110 is determined. The end effector frames 116 are fixed relative to the world frame 14C at the cart 20, since the end effectors 60, 60 are locked in position and orientation. The camera frame 110 position and orientation relative to the world frame at the cart 20 is determined by means of the sensors associated with the camera arm 22. Accordingly, the camera frame 110 position and orientation relative to the fixed end effector frames 116, 116 (which are fixed relative to the world frame 14C) can readily be determined. This is achieved at 260. To achieve this, the positions and orientations of the end effector frames 116, 116 relative to the world reference frame 14C is input to 260 from 262. Furthermore, sensed angular positions of the arm portions of the camera arm 22 about its pivotal connections are input as indicated at 260A from a memory 261. It will be appreciated that from the information from 261, 262 the position and orientation of the camera frame 110 relative to the positions of the end effector frames 116, 116 is determined at 260.

At 258, the velocity of the end effector frames 116, 116 relative to the camera frame 110 which is required to "catch up" to the positions and velocities of the scaled and offset positions and velocities of the master frames 158, 158 relative to the world frame 14B is determined. Since the end effector frames 116, 116 are fixed, a resultant camera frame 110 velocity relative to the fixed end effector frames 116, 116 to "catch up" to the positions and velocities of the master frames 158, 158 relative to the world reference frame 14B is determined at 264. This velocity is then input to 266.

Figure 12:
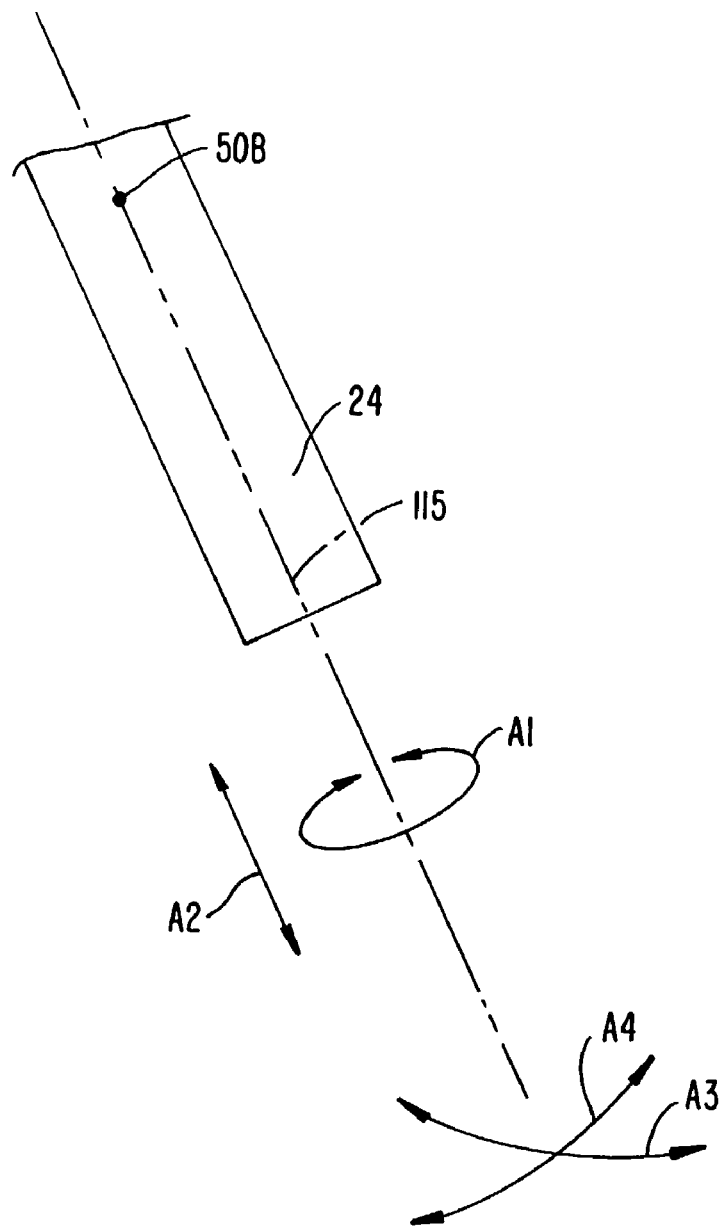
FIG. 12 shows a schematic view of a viewing end of an endoscope of the system and indicates freedoms of movement of the endoscope.
Figure 14:
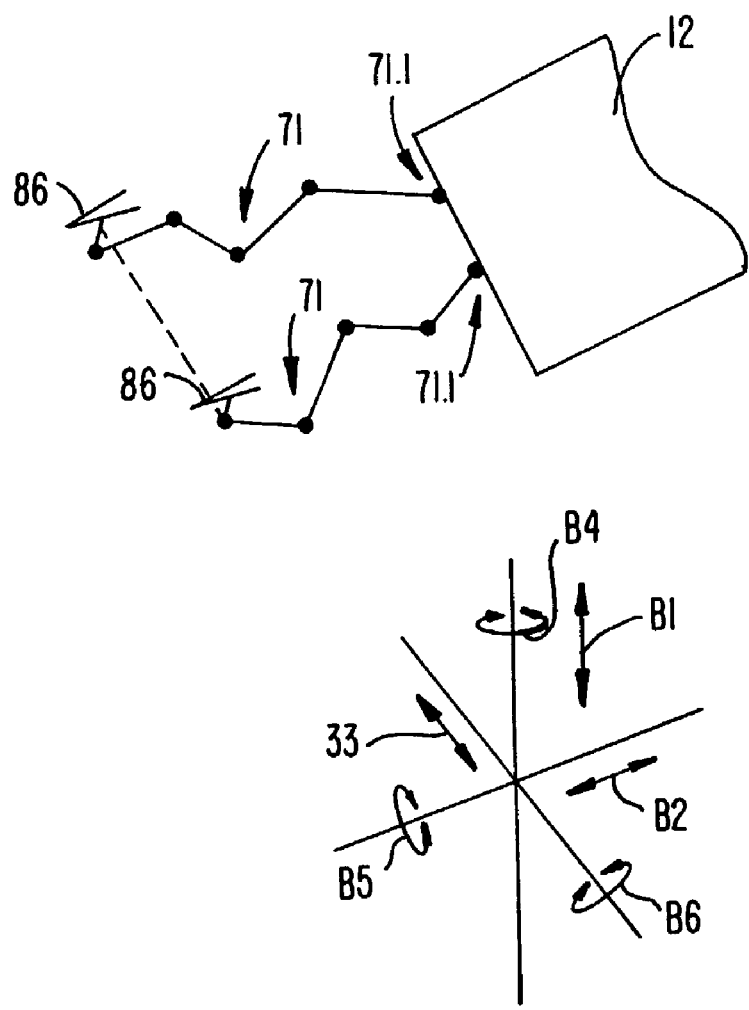
FIG. 14 shows a schematic view of the master controls and indicates freedoms of movement of the hand-grippable parts of the master controls relative to opposed ends of master arms of the master controls on which the hand-grippable parts are mounted.

As described with reference to FIG. 12, the endoscope 24 has four degrees of freedom of movement. The hand-grippable parts 86, 86 when locked together have six degrees of freedom of movement relative to the opposed ends 71.1, 71.1 of the master arms 71, 71, as indicated schematically in FIG. 14. These six degrees of freedom of movement are indicated by arrows B1, B2, B3, B4, B5 and B6 in FIG. 14.

At 266, the velocity of the camera frame 110 relative to the fixed end effector frames 116, 116 is restricted to a velocity which is achievable by the endoscope 24 relative to the opposed end 22.1 of the camera arm 22 within its four available degrees of freedom of movement.

The resultant camera frame 110 velocity relative to the end effector frames 116, 116 is then forwarded to 268. At 268, corresponding "joint space" commands or actuator command signals are determined for causing the actuators associated with the camera arm 22 to drive the endoscope 24 in conformity with the determined camera frame 110 velocity relative to the fixed end effector frames 116, 116.

The "joint space" commands are then forwarded to 270. It will be appreciated that the endoscope has a limited range of movement within each of its four degrees of freedom of movement. At 270, the joint space command signals are restricted if they would cause the endoscope 24 to be moved beyond any one of its ranges of movement within its four degrees of freedom of movement, so as to provide joint space command signals which would not cause infringement of any one of the ranges of movement. This is achieved by taking the angular positions of the camera arm portions about its pivotal connections into account, from the memory 261, as indicated by branches 266A, 268B and 270B.

The resultant joint space command signals are then forwarded to 274 via branch 276. At 274, the joint space command signal, which is in the form of a joint space velocity, is integrated to obtain new "angular positions" for updating the memory 261, via branch 280. Accordingly, memory 261 can keep track of the angular positions of the arm portions of the camera arm 22 about its pivotal connections. This updated information 261 is then used in the blocks 266, 268, 270 as indicated by branches 266A, 268B and 270B.

It will be appreciated that during such an endoscope movement, to change the displayed image at the image display 14, the control system path defined from 258 to 264, from 264 to 266, from 266 to 268, from 268 to 270, from 270 to 274, and from 274 to 261, from 261 to 260, and from 260 back to 258 is followed cyclically, typically at 1300 Hz, and, accordingly, is constantly adapting to new inputs from 250 and 256 in response to hand-grippable part 86, 86 movement and changes in position of the endoscope 24 relative to the locked end effectors 60, 60.

From 274, the joint space position is input to 282 via branch 284. From 272, the joint space velocity is also input to 282 via branch 286. At 288, the angular positions of the arm portions of the camera arm 22 about its pivotal connections as sensed by the sensors associated with the camera arm 22 is input as indicated by 290. At 288, the sensed information is used to determine actual endoscope velocity and position. The actual endoscope velocity and position is input to 282 as indicated by branches 292, 294. At 282, the actual endoscope position and velocity inputs 292, 294 are compared with the commanded endoscope position and velocity from 284, 286 to yield a resultant torque which is communicated to the actuators associated with the camera arm 22 to cause the actuators to drive the endoscope into a corresponding position as indicated by arrow 296.

The restricted joint space velocity is also passed from 270 to 298 as indicated by branch 272. The joint space velocity is converted back into "Cartesian space" at 298. At 300, the corresponding Cartesian space velocity, which corresponds to a velocity of the camera frame 110 relative to the fixed end effector frames 116, 116 is converted into a corresponding master frame 158, 158 velocity relative to the eye frame 150. This velocity, is then forwarded to a scale and offset step at 302 together with end effector frame 116 positions relative to the camera frame 110 from 260.

It will be appreciated that at 302, a scale and offset step is performed in a manner opposite to the scale and offset step at 256. The resultant Cartesian space velocity and position of the master frames 158, 158 relative to the eye frame 150, or world frame 14B, is then input to 306.

At 306, the master Cartesian space position and velocity from 250 as commanded by the surgeon is input as indicated by 308, 310. At 306, the information from 302 and 250 is compared. In the event that the position and velocity as commanded by the surgeon was restricted at 266, 270, appropriate torque is transmitted to the actuators associated with the master controls 70, 70 to resist hand-grippable part 86, 86 movement commands, which infringe the available ranges of motion within the possible degrees of freedom of movement. In this manner, the surgeon is provided with force feedback and "feels" when "illegal" commands are input.

Figure 15A:
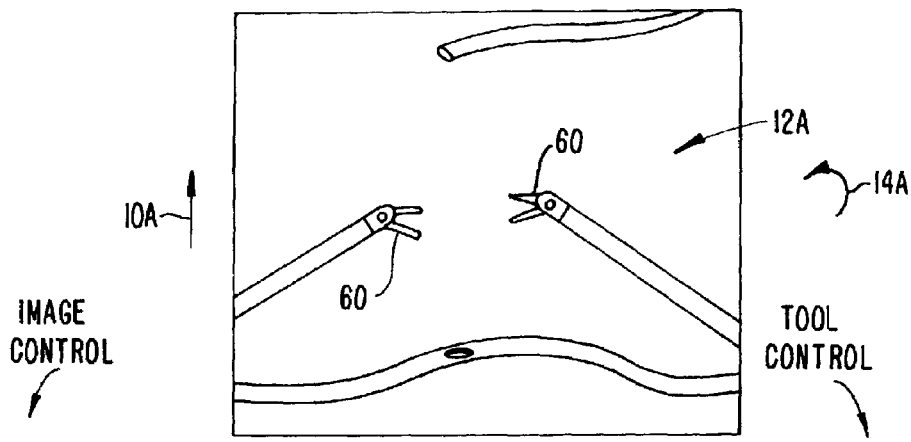
FIGS. 15A-15D show schematic representations of an image viewed by a surgeon on an image display of the telesurgical system, the image revealing the two remote surgical instruments, which the surgeon is manipulating via the two master controls, in the performance of a surgical procedure.
Figure 15B:
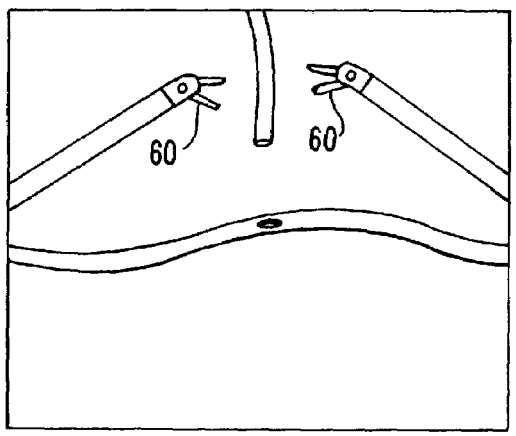

Causing the displayed image to change in accordance with the algorithm 200 will now be described with reference to FIGS. 15A to 15D of the drawings. If the surgeon wishes to change the displayed image on the image display 14, such as to change the image as shown in FIG. 15A by causing it to move in the direction indicated by arrow 10A, the surgeon can accomplish this by actuating the suitable input. Once the suitable input is actuated, operative association between the master controls 70, 70 and the displayed image, as indicated at 12A in FIG. 15A, is established. This is achieved by operatively associating the master controls 70, 70 with the endoscope 24. The surgeon can then move the hand-grippable portions 86, 86 in the same direction as arrow 10A thereby to cause the endoscope 24 to be displaced so as to capture the image indicated in FIG. 15B, ideally while the control system moves the endoscope so that the image, including the image of any tissues and the image of the instrument or instruments appear to remain at least substantially connected to the hand-grippable part(s). In similar fashion, if the surgeon wishes to rotate the image 12A as indicated by arrow 14A, the surgeon can simply displace the locked together hand-grippable parts 86, 86 in a direction corresponding with arrow 14A so as to cause the endoscope 24 to displace angularly about its axis 115 thereby to cause the displayed image 12A to change as indicated in FIG. 15C, ideally while the control system maintains at least substantial and orientational connection between the master controller and image.

Figure 15D:
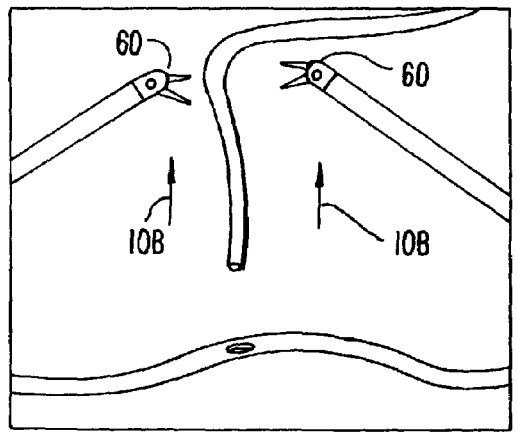
Figure 15C:
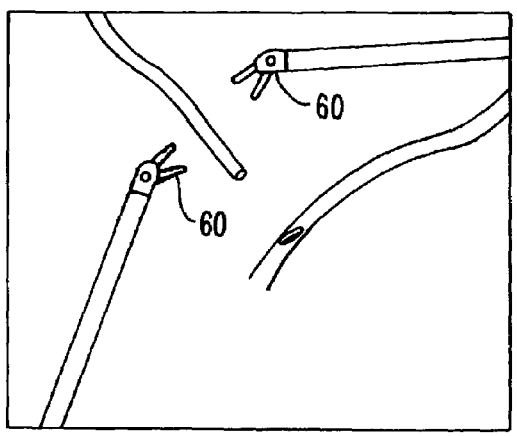

By way of example, and with reference to FIG. 15D, if the hand-grippable parts 86, 86 were moved in the direction of arrow 10A while the master controls 70, 70 were still operatively associated with the end effectors 60, 60, the end effectors 60, 60 would have been caused to move in the direction 10A relative to the surgical site as indicated by the arrows 10B in the displayed image 12B in FIG. 15D.

Accordingly, if the surgeon wishes an image shift from the image represented in FIG. 15A to the image represented in FIG. 15B, he can depress the foot pedal, if the selection input is in the form of a foot pedal, and can then move the hand-grippable parts 86, 86 in an upward direction or X direction relative to the image display 14 whilst looking at the surgical site as displayed on the image display 14. Operative association between movement of the hand-grippable parts 86, 86 and responsive movement of the endoscope 24 is typically immediately established when the foot pedal is depressed. Accordingly, the surgeon can then move the hand-grippable parts 86, 86 until the desired image, e.g., the image shown in FIG. 15B, is displayed on the image display 14. Thus, an image shift of the displayed image in the direction of arrow 10A is then achieved. In FIG. 15C, counter clockwise movement of the hand-grippable parts 86, 86 effects movement of the endoscope so that the displayed image of the surgical site appears to the surgeon to follow movement of the hand-grippable parts 86, 86 in the anti-clockwise direction. This movement of the image can also be provided in additional degrees of freedom, by having the image zoom in when the hand-grippable parts move toward the operator's eyes, by tilting the image corresponding with a tilting movement of the hand-grippable parts relative to the operator's eyes, and the like.

Conveniently, when operative association between the displayed image and the master controls 70, 70 is established upon actuation of the suitable input, the orientation of each hand-grippable part 86, 86 relative to its associated end effector 60, 60 is locked relative to each other. This provides beneficial results. In practice, when the surgeon performs such a change in the displayed image, intuitive control between the master 70, 70 and the end effector 60, 60 is preserved during such a change in displayed image. Since the orientations of the hand-grippable parts 86, 86 are locked relative to the orientations of the end effectors 60, 60, and the hand-grippable parts 86, 86 are locked in position relative to each other, and the end effectors 60, 60 are locked in position and orientation, during such image change, effective alignment or mapping between the hand-grippable parts 86, 86 and the end effectors 60, 60 is preserved after such an image change operation is performed. This enhances the surgeon's intuitive "feel" when performing a surgical procedure by means of the system 10 during such a change in displayed image.

As mentioned earlier, the hand-grippable parts 86, 86 when locked relative to each other during such an image change, have six degrees of freedom of movement. The endoscope 24 only has four degrees of freedom of movement. Accordingly, it is possible that the two "redundant" degrees of freedom of movement of the hand-grippable parts 86, 86 may be employed to perform other functions during an image change operation. For example, one of the redundant degrees of freedom of movement may be used to vary the focus of the endoscope 24.

Advantageously, when the hand-grippable parts 86, 86 are locked relative to each other during an image change operation, they are not rigidly locked together but resiliently locked together. Thus, the hand-grippable parts 86, 86 are then resiliently held relative to each other during an image change operation. The resiliently variable position of the hand-grippable parts 86, 86 relative to each other can then be used to perform other functions during an image change operation. For example, should the surgeon then urge the hand-grippable parts away from each other, the focus of the endoscope 24 can be varied in one direction, and when the surgeon urges the hand-grippable parts toward each other, the focus of the endoscope 24 can be varied in an opposed direction. Instead, zooming can be effected in similar fashion. This can typically be achieved by linking relative movement of the hand-grippable parts 86, 86 relative to each other, to an actuator, such as an electric motor, operatively coupled with displaceable lenses in the endoscope 24.

In the description above, the master controls 70, 70 were freed from their operative association with the end effectors 60, 60. A method of changing the image on the image display 14 comprising moving the endoscope in response to movement of both hand-grippable parts 86, 86 was described. It will be appreciated that the same results in moving the endoscope 24 can be achieved by using a single master control 70. This will now be described.

Figure 17:
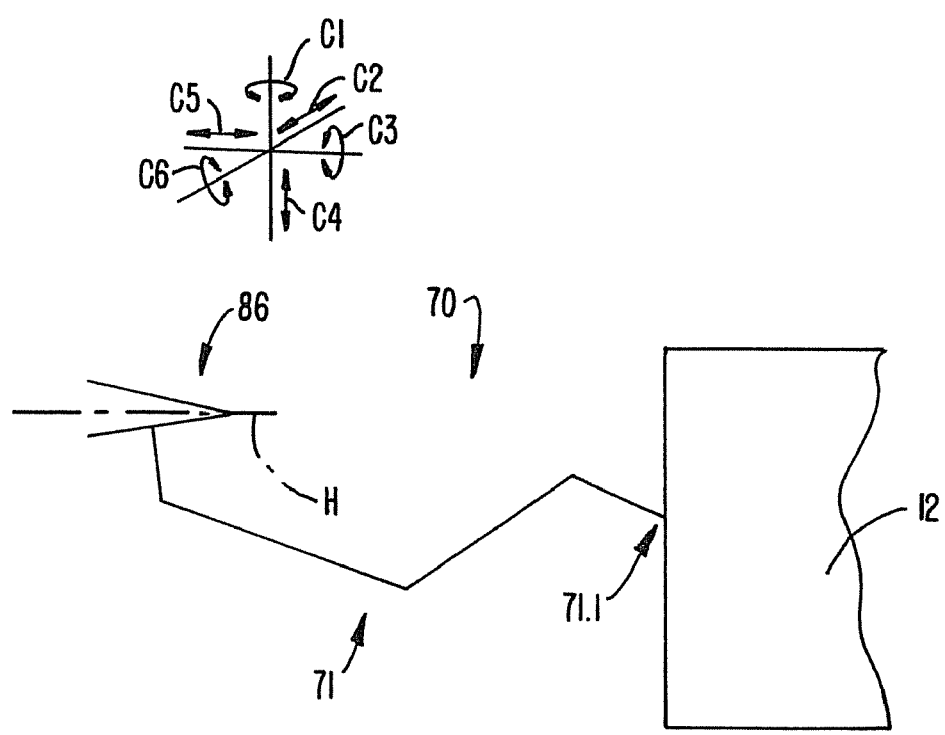
FIG. 17 shows a schematic diagram indicating freedoms of movement of a hand-grippable part of a master control relative to an opposed end of a master arm on which it is mounted.

In such a case, for example, upon actuation of the selection input, one of the masters can be locked in position, while the other master 70 is operatively associated with the endoscope 24. Referring to FIG. 17, each master 70 typically has six degrees of freedom of movement. These degrees of freedom of movement are indicated schematically by arrows C1, C2, C3, C4, C5 and C6. As already mentioned, the endoscope 24 only has four degrees of freedom of movement. Accordingly, four of the degrees of freedom of movement of the hand-grippable part 86 of the freed master 70 to be used to change the position of the endoscope 24 can be used for causing responsive movements of the endoscope within its four degrees of freedom of movement. This can leave two redundant degrees of freedom of movement at the master. As mentioned above, the redundant degrees of freedom of movement can be used for other purposes, such as to effect focus, or zooming, or the like. When a single master 70 is used in this fashion, angular displacement of the hand-grippable part 86 about its roll axis as indicated at H can conveniently effect corresponding angular displacement of the endoscope 24 about its axis 115.

Figure 16A:
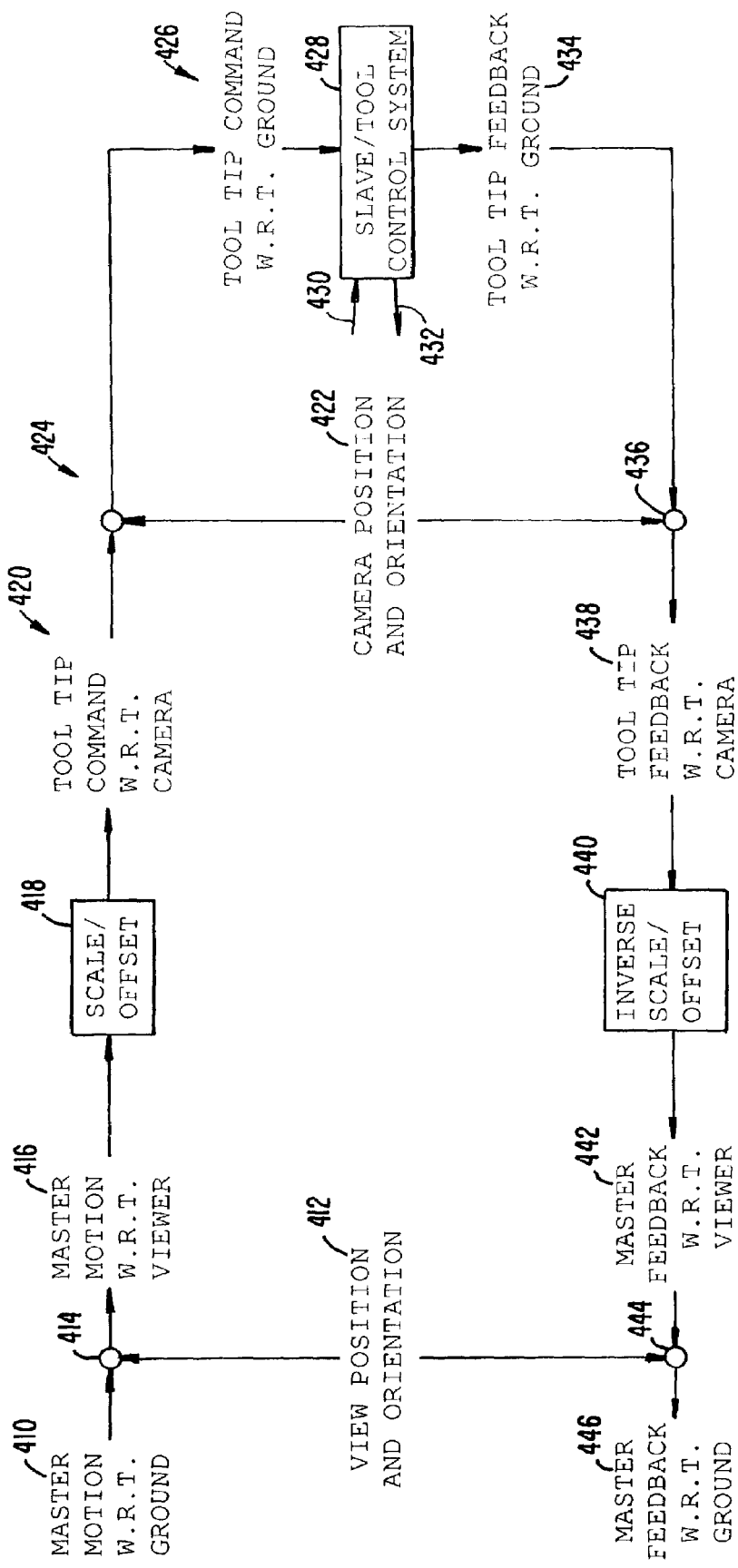
FIG. 16A shows a flow diagram indicating control steps employed when end effectors are operatively associated with the master controls and the end effectors are caused to perform movements in response to master control input.
Figure 16B:
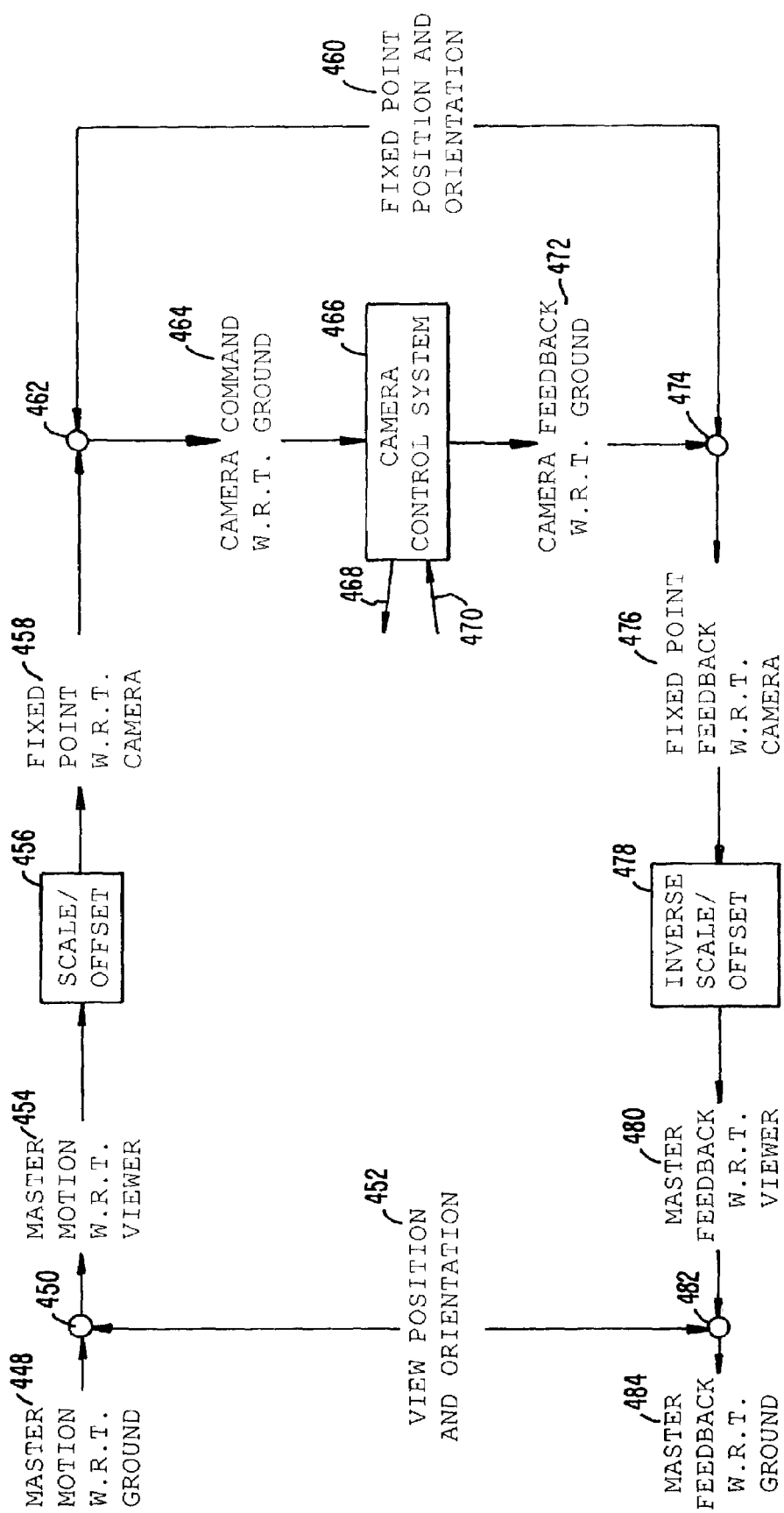
FIG. 16B shows a flow diagram which corresponds to FIG. 16A and shows control steps employed when an endoscope is operatively associated with one, or both, master controls, and the endoscope is caused to move in response to master control input.

Referring now to FIGS. 16A and 16B, another method of performing an image change on the displayed image 14 by means of causing the endoscope 24 to displace relative to the surgical site will now be described.

In FIG. 16A, association between one, or both, master controls and its, or their, end effector or end effectors will now be described. The master frame motion with respect ground or to the appropriate world frame at the surgeon's console 12 is indicated at 410. It will be appreciated that the master frame motion can correspond to master frame motion of a single master control 70 or it can correspond with motion of both master frames relative to the appropriate world frame. The position and orientation of the eye frame 150 relative to the world frame is indicated at 412. At 414, the values from 410 and 412 are compared to determine master frame motion relative to the eye frame 150 as indicated at 416. The values from 416 are then passed through a scale and offset block 418 to provide a corresponding end effector frame motion with respect to the camera frame 110. This is indicated at 420. The position and orientation of the camera frame 110 relative to an appropriately attached world frame on the cart 20 is indicated at 422. At 424, the values from 420 and 422 are compared to determine end effector frame 116 motion relative to ground or the world reference frame on the cart 20, as indicated at 426. The information from 426 is then input to block 428. Block 428 schematically indicates a control block which determines corresponding actuator command signals to drive the end effector, or end effectors, to a position and orientation dictated by the values from 426. It will be appreciated that up until 426 the relevant motions were determined in Cartesian space. The output from 428 to the actuators associated with the instrument arm, or arms, 26, 26, is indicated by arrow 430 and is in joint space. It could happen that the commands 430 cause the end effector(s) to, for example, collide with an object at the surgical site. In such a case, joint space information is fed into 428 as indicated by arrow 432 to provide for force feedback. This information is then transferred into Cartesian space to define end effector frame 116 feedback motion with respect to the world frame, as indicated at 434. The information from 434 is then passed to 436 where it is compared with information from 422 to yield end effector frame feedback motion with respect to the camera frame 110, as indicated at 438. The information from 438 is then fed to an inverse scale and offset step as indicated at 440. From 440, a corresponding master frame feedback motion with respect to the eye frame 150 is determined as indicated at 442. At 444, the information from 442 is compared with information from 412 to yield Cartesian space master frame feedback motion with respect to the world frame, as indicated at 446.

The description above with reference to FIG. 16A corresponds to operative association between one, or both, of the masters and an associated end effector or end effectors.

Referring to FIG. 16B, and upon actuation of a suitable input, moving the endoscope 24 relative to the surgical site to change the image displayed on the image display 14 will now be described. In FIG. 16B the master frame motion with respect to the world frame is indicated at 448. This information is compared at 450 with the position and orientation of the eye frame 150 relative to the world frame as indicated at 452. From the comparison at 450, master frame motion relative to the eye frame 150 is determined as indicated at 454. Information from 454 is passed through a scale and offset step 456 to yield a corresponding end effector frame motion relative to the camera frame 110 as indicated at 458. As mentioned, upon actuation of the selection input, the end effectors are locked in their positions and orientations. The positions and orientations of the fixed end effector frames relative to the world frame on the cart 20 is indicated at 460. The information from 458 and 460 is compared at 462. From the comparison at 462, a desired camera frame 110 motion relative to the world reference frame at the cart 20 is determined as indicated at 464. The information at 464 is passed to a camera control system as indicated at 466 where corresponding actuator command signals are computed and forwarded to the actuators associated with the camera arm 22 to drive the camera arm to move the endoscope accordingly. These actuator command signals are indicated by the arrow 468. For force feedback as indicated by arrow 470, the sensors operatively associated with the camera arm 22 cause camera feedback motion relative to the world frame to be computed as indicated at 472. At 474, the information from 472 is compared with information from 460 to yield a corresponding motion of the end effector frame relative to the camera frame 110 as indicated at 476. The information from 476 is fed through an inverse scale and offset block as indicated at 478. From 478, a corresponding master feedback motion relative to the eye frame 150 is determined as indicated at 480. At 482, the information from 480 is compared with the information from 452 to yield a master feedback motion with respect to the world frame attached to the console 12 as indicated at 484.

Expressed differently, in FIGS. 16A, 16b, normal operation is contrasted with an image change or shifting mode. FIG. 16A shows the basic control system layout for normal operation, where the master controls are operatively connected to the end effectors. Sensors on the master controls 70, 70 determine the master motion with respect to ground 410. This is combined with the view location 412, including position and orientation, to provide the master motion with respect to the viewer at 416. After processing by a scale and offset at 418, this provides the end effector command with respect to the camera at 420. After combining with the current camera location 422, including position and orientation, this provides the end effector command with respect to the world frame and/or fixed ground at 426. The slave control system 428 then forces the end effectors to follow this command. In the feedback portion of the system, the end effector feedback position with respect to the fixed space at 434 is also adjusted for the current camera location 422 to provide a feedback position with respect to the camera 438. An inverse scale and offset at 440 provide the master feedback position 442 with respect to the viewer. The view location 412 allows adjustment to provide the actual feedback signals for the master motors at 446.

FIG. 16B shows the analogous layout for image shifting. Instead of associating the master controls with the end effectors, they are associated with fixed image points. The tool tip command is replaced by the analogous fixed image point motion command 458 with respect to the camera. The fixed point locations 460 are used to determine actual camera motion commands 464, which are supplied to the camera control system 466. The camera feedback position 472 is combined with the fixed point locations 460 to provide fixed point feedback motions 476, which are analogous to the end effector feedback motions 438, and are directed to the master motors via the inverse scale and offset 478.

The camera control system 466 is aware of the physically achievable motions and will only follow commands which fall into this category. As a result, the feedback position will prevent the master controls from moving in directions that are not consistent with the possible camera movements. In particular, the fixed distance between the two master controls is achieved via this mechanism.

Typically, the image fixed points will be selected to match the end effector locations. However, when operating without tools or if otherwise desired, the fixed points may be located at other locations in front of the camera so that they are connected to the visible image.

As can be seen, end effector control and image change function in similar fashion so as to enable the task of changing the image to be performed with relative ease by the surgeon. This is achieved by using one or both of the masters as positional and orientation input devices for both controlling end effector movement as well as changing the image. It will also be appreciated that both, or one, of the masters can also be used differently, for example, as rate controllers.

Figure 18:
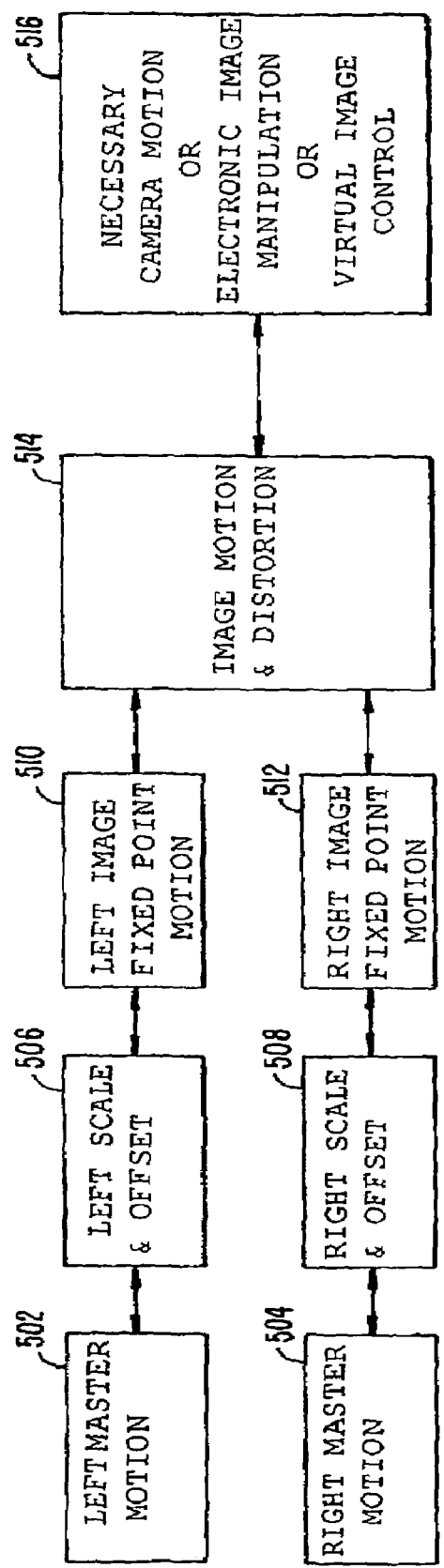
FIG. 18 shows a schematic diagram indicating control steps employed to change an image displayed on an image display.

The operative association between the master controls 70, 70 and changing the displayed image will now be described with reference to FIG. 18. The motion of one of the master controls 70, which includes its position, orientation, and velocity, is indicated at 502. After processing by a scale and offset step at 506, this motion determines the desired motion of an image fixed point one, as indicated at 510. Similarly, the motion of the other master control 70 as indicated at 504 is processed by a scale and offset step at 508 to provide the motion of an image fixed point two, as indicated at 512. Together, motions 510 and 512 determine the total image motion and possible distortion at 514. This image motion is then processed into a corresponding camera motion or electronic image change as indicated at 516.

Changing the image as described above, by means of one or both masters, can be used to change the image on the image display 14 in a number of different ways. One such way is by moving the endoscope 24 as already described. It will be appreciated that the image may be changed in other ways as well. One such way is electronically. For example, causing electronically regulatable information associated with the captured image to be regulated in response to master control input can provide for zooming into a smaller portion of the displayed image or for panning (or selectively cropping) a small view inside a larger image. The change in the image is typically described by a motion of the image, which can include position, orientation, and velocity. In addition, or instead, it may also be described by a distortion, for example, a zoom, change in horizontal scale, change in vertical scale, or an angular distortion reshaping a rectangular view into a parallelogram view or a trapezoidal view, or the like.

Relating this total image motion and distortion at 514 to the actual manipulation control at 516 is achieved by rules of manipulation. Typically, when limiting image manipulation to motion of the camera, the motion of the camera in fixed space is simply the opposite of the motion of the image in the viewer. For example, moving the image left is achieved by moving the camera right by typically an equal amount.

While one master control 70 is sufficient to command the image motion, the preferred embodiment, as described above, uses both masters. For simple image motions, including translations and rotations, the two masters 70, 70 are operatively connected to two fixed points relative to each other. However, they are free to move in Cartesian space so that they appear as if attached by a rigid body. This apparent rigid body is thus operatively associated with the displayed image to change the image in response to movement of the "virtual" body. As mentioned above, where the hand-grippable parts 68, 68 are resiliently locked relative to each other, image distortion in the form of zooming, or scaling, can be effected by changing the distance between the hand-grippable parts 68, 68, thereby to change the image in zoom, or scale, or the like. For example, pulling the hand-grippable parts 68, 68 apart may indicate a larger zoom factor or scale factor if desired and the image should be enlarged.

Figure 19:
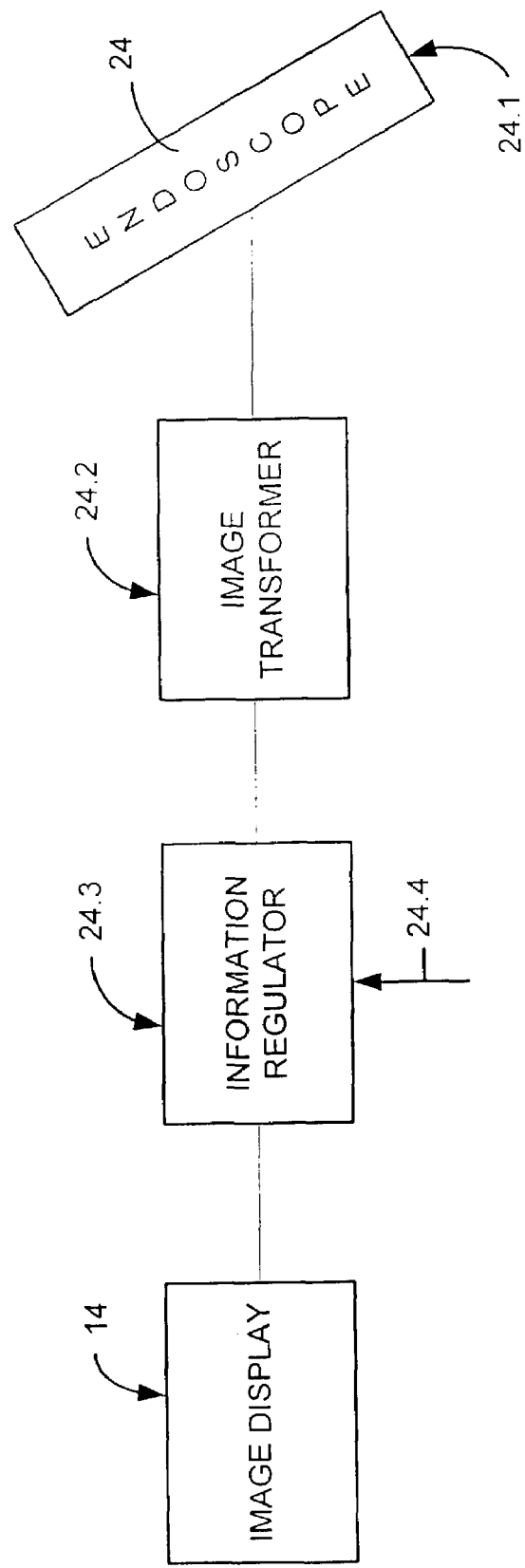
FIG. 19 shows a schematic diagram indicating a path along which an image captured by the endoscope is passed to the image display.

Referring now to FIG. 19 of the drawings, the image display is indicated schematically at 14 and the endoscope is indicated schematically at 24. As mentioned, the endoscope 24 is operatively linked to the image display 14 so as to display an image captured at its viewing end 24.1 on the image display 14. Advantageously, the captured image can be transformed into regulatable information, such as digital information, as indicated at 24.2. The information corresponding to the captured image, after having been changed into regulatable information at 24.2 is then passed to a information regulator at 24.3. From the information regulator 24.3 the information is passed to the image display 14 so that the captured image is displayed thereon. In accordance with another aspect of the invention, upon actuation of the selection input, and consequently the disassociation of one or both masters from the end effectors 60, 60, the one or both masters are then free to be used to change the displayed image on the image display 14. As described above, the change in image can be achieved by means of moving the endoscope 24. Instead, the displayed image can be changed by operatively associating movement of one, or both, masters 70, 70 with the information regulator 24.3, as indicated schematically by arrow 24.4. Thus, the information corresponding to the captured image at 24.3 can be regulated in response to movement of the one, or both, masters 70, 70. It will be appreciated that specific directional movements of the hand-grippable parts 86, 86 relative to the opposed ends 71.1, 71.1 of their arms 71, 71 can be used to regulate the regulatable information in a specific manner at 24.3. Accordingly, the information can be regulated to cause the displayed image to for example, shift, rotate, zoom, pan, and/or the like.

It will be appreciated that after the image change operation has been performed, the connection or association between the masters and end effectors can be restored. In this regard, refer to Applicant's co-pending U.S. patent application Ser. No. 09/287,858, entitled "Alignment of Master and Slave in a Minimally Invasive Surgical Apparatus," filed Apr. 7, 1999, and/or to U.S. patent application Ser. No. 09/398,960, entitled "Repositioning and Reorientation of Master/Slave Relationship in Minimally Invasive Telesurgery," filed Sep. 17, 1999, the full disclosures of which are incorporated herein by reference.

Using the master for dual functions, as described above, is the preferred method for enabling image change or shifting. It will be appreciated, however, that separate master controllers may be dedicated to image shifting. Accordingly, the system 10 may be provided with a dedicated input device used to change the displayed image. Such a device can be in any appropriate form and can be in the form of a master control similar to the master controls 70, 70.

The master controls 70, 70, when locked together, as described above, preferably move as a contiguous body, thereby defining a single movable position and orientation in the control station workspace 18. Hence, the two locked master controls can be moved together as a single master controller system to effect positional and orientational adjustments of the image viewed by the surgeon. As mentioned, a single master control with position and orientation capabilities (typically having six degrees of freedom) may be used. Nonetheless, the use of two controllers is preferred, as it gives the surgeon the impression of grabbing and repositioning the surgical workspace viewed by the camera with both hands.

Advantageously, as described above, the alignment between the master controls 70, 70 and the end effectors 60, 60 during image change is maintained, as well as during normal operation, to provide smoother/faster/more precise operation and assures that the end effectors are not accidentally "lost" during image change.

In general, these improved teleoperator techniques often make use of at least one input device which can be selectively operatively associated with, for example, either a surgical instrument to treat tissues, or with an image of a surgical worksite shown to a system operator. A novel image manipulation arrangement effects movement of the image corresponding to the movement of the input device so that the image appears substantially connected to the input device, optionally while the instrument (or instruments) remain at a fixed location at the worksite. This can give the operator the appearance of grasping and/or manipulating target tissue and worksite into a desired position for viewing, while movement of the image is actually effected by repositioning of the image capture device, electronic image manipulation, or the like. Alternative embodiments may make use of dedicated input devices for the image capture device and the instrument, and these image manipulation and teleoperator techniques will find uses in industrial, hazardous environment, and other applications.

The exemplary embodiment of the method and structure of the invention has been described in some detail for clarity of understanding. As changes and modifications will be obvious to those of skill in the art in light of the description, the scope of the invention is limited solely by the following claims.

What is claimed is:

1. A method of using a robotic system, the method comprising:
   displaying an image of a worksite on an image display;
   causing an end effector to move in response to operator manipulation of a master control when the end effector is operatively associated with the master control;
   receiving an indication that operative association of the master control has been switched from the end effector to an image control; and
   causing the displayed image to be altered so as to provide a different view of the worksite without moving the end effector in response to operator manipulation of the master control.

2. A robotic system comprising:
   an image capturing device for capturing an image of a worksite;
   an image display coupled to the image capturing device for displaying the captured image;
   an end effector;
   a master control; and
   a control system configured to switchably associate the master control between the end effector and the image capturing device so as to cause the end effector to move in response to manipulation of the master control when the end effector is associated with the master control and cause the displayed image to be altered without moving the end effector in response to manipulation of the master control when the image capturing device is associated with the master control.

3. The system as claimed in claim 2, further comprising: a selection input, the selection input being selectively actuatable to switch operative association between either the master control and the end effector or the master control and the image capturing device.

4. The system as claimed in claim 3, further comprising: a camera arm defining opposed ends, the image capturing device being mounted at one end of the camera arm.

5. The system as claimed in claim 4, wherein the master control includes a master arm with a hand-grippable part at one end and an opposed end, and wherein the control system is configured to switchably associate the master control with the image capture device so as to cause the image capture device to be displaced relative to the opposed end of the camera arm in response to movement of the hand-grippable part relative to the opposed end of the master arm, thereby to cause the image captured device to move relative to the worksite so as to alter the displayed image.

6. The system as claimed in claim 5, wherein the control system defines a camera reference frame attached relative to a viewing end of the image capture device and a world reference frame attached relative to the opposed end of the camera arm.

7. The system as claimed in claim 6, further comprising: camera arm sensors operatively associated with the camera arm, wherein the control system is configured to determine the location of the camera reference frame relative to the world reference frame from the camera arm sensors.

8. The system as claimed in claim 7, wherein the control system defines a master reference frame attached relative to the hand-grippable part and a world reference frame attached relative to the opposed end of the master arm.

9. The system as claimed in claim 8, further comprising: master arm sensors associated with the master arm, wherein the control system is configured to determine the location of the master reference frame relative to the world reference frame from the master arm sensors.

10. The system as claimed in claim 9, wherein the control system is arranged to compare the location of the camera reference frame relative to the world reference frame with the location of the master reference frame relative to the world reference frame.

11. The system as claimed in claim 10, wherein the control system is configured to compare a position of the camera reference frame relative to the world reference frame with a position of the master reference frame relative to the world reference frame.

12. The system as claimed in claim 10, wherein the control system is configured to compare an orientation of the camera reference frame relative to the world reference frame with an orientation of the master reference frame relative to the world reference frame.

13. The system as claimed in claim 10, further comprising: actuators associated with the camera arm for driving the image capture device to displace relative to the opposed end of the camera arm.

14. The system as claimed in claim 13, wherein the control system is configured to generate actuator command signals if the location of the camera reference frame relative to the world reference frame does not correspond with the location of the master reference relative to the world reference frame, the actuator command signals being generated so as to cause the actuators to drive the image capture device into a location in which the location of the camera reference frame relative to the world reference frame would correspond with the location of the master reference frame relative to the world reference frame in terms of a predetermined locational relationship between the camera reference frame relative to the world reference frame and the master reference frame relative to the world reference frame.

15. The system as claimed in claim 2, further comprising: a second master control, wherein each of the master control and the second master control includes a master arm defining opposing ends and a hand-grippable part mounted on one of the ends of the master arm, and the control system is configured to cause the displayed image to be altered in response to moving both hand-grippable parts relative to the opposed ends of the master arms.

16. The system as claimed in claim 15, wherein the control system is configured to inhibit movement of the hand-grippable parts relative to each other so as to cause the displayed image to be altered in response to moving both hand-grippable parts relative to the opposed ends of the master arms while movement of the hand-grippable parts relative to each other is inhibited.

17. The system as claimed in claim 16, wherein the control system defines a master reference frame attached relative to the hand-grippable parts and a world reference frame attached relative to the opposed ends of the master arms.

18. The system as claimed in claim 17, wherein the control system is configured to move the master reference frame relative to the world reference frame in response to sensors of the master arms sensing movement of the hand-grippable parts relative to opposed ends of the master arms.

19. The system as claimed in claim 15, further comprising: a second end effector, wherein the control system is configured to associate the end effector and the second end effector with the master control and the second master control to enable each of the end effectors to be moved in response to movement of the hand-grippable part of the associated master control.

20. A telerobotic system comprising:
  a viewer;
  a camera positionable at a remote site, the camera mounted on a robotic arm to enable it to be positionally adjustable at the remote site, and being operatively associated with the viewer to enable an image of the remote site to be displayed on the viewer;
  a slave instrument or tool positionable at the remote site, the tool being mounted on a robotic arm to enable it to be worked at the remote site;
  a master control device positioned in close proximity to the viewer to enable it to be manipulated by a user of the system whilst the user is viewing the remote site through the viewer, the master control device further being arranged selectively to establish control with the robotic arm of the camera and the robotic arm of the slave instrument, so that position adjustment of the camera and working of the tool can be effected by the master control.

21. A method implemented in a robotic system including a viewer and at least two master control devices, the viewer operatively associated with a remote camera arrangement so as to display an image viewed by the camera on the viewer, each of the at least two master control devices operatively connected to a remote instrument or tool so as to cause displacement of the instrument or tool in response to displacement of its associated master control device, the method for shifting the image relative to the instruments, the method comprising:
  locking the instruments at stationary positions;

switching operative association of the master control devices from the instruments to the camera;
moving the master control devices relative to the viewer whilst movement of the master control devices relative to each other is restrained; and
causing the camera to displace relative to the instruments, whilst the instruments are held at their stationary positions, in response to the master control devices displacing relative to the viewer.

22. A method implemented in a minimally invasive surgical system including a viewer and two master control devices, the viewer operatively associated with an endoscope, each of the two master control devices operatively associated with at least one corresponding slave instrument, the method for shifting an image viewed through the viewer relative to the instruments, the method comprising:
locking the slave instruments at stationary positions;
switching operative association of the two master control devices from the slave instruments to the endoscope;
moving the two master control devices relative to the viewer whilst the two master control devices are held at fixed positions relative to each other; and
causing the endoscope to displace relative to the slave instruments, whilst the slave instruments are held at their stationary positions, in response to the two master control devices displacing relative to the viewer.

23. A robotic system comprising:
an image capturing device for capturing an image of a worksite;
an image display coupled to the image capturing device for displaying the captured image;
an image transformer for transforming the captured image into regulatable information;
an information regulator for regulating the regulatable information so as to enable the displayed image to be altered;
an end effector;
a master control; and
a control system configured to switchably associate the master control between the end effector and the information regulator so as to cause the end effector to move in response to manipulation of the master control when the end effector is associated with the master control and cause the displayed image to be altered without moving the end effector in response to manipulation of the master control when the information regulator is associated with the master control.

24. The system as claimed in claim 23, wherein the control system is configured to associate the master control with the information regulator so as to cause the information regulator to regulate the regulatable information in response to movement of a hand-grippable part of the master control.

25. The system as claimed in claim 24, wherein the master control includes a master arm with the hand-grippable part at one end and an opposed end, wherein the hand-grippable part is positionally adjustable relative to the opposed end of the master arm, wherein the control system defines a master reference frame attached relative to the hand-grippable part and a world reference frame attached relative to the opposed end of the master arm, the control system configured to change a position of the master reference frame relative to the world reference frame in response to sensing movement of the hand-grippable part relative to the opposed end of the master arm, and wherein the control) system is configured to cause the information regulator to regulate the regulatable information in response to changing position of the master reference frame relative to the world reference frame.

26. The system as claimed in claim 24, wherein the master control includes a master arm with the hand-grippable part at one end and an opposed end, wherein the hand-grippable part is orientationally adjustable relative to the opposed end of the master arm, wherein the control system defines a master reference frame attached relative to the hand-grippable part and a world reference frame attached relative to the opposed end of the master arm, the control system configured to change an orientation of the master reference frame relative to the world reference frame in response to sensing movement of the hand-grippable part relative to the opposed end of the master arm, and wherein the control system is configured to cause the information regulator to regulate the regulatable information in response to changing orientation of the master reference frame relative to the world reference frame.

* * * * *